(12) United States Patent
Lopez Camacho et al.

(10) Patent No.: US 12,605,192 B2
(45) **Date of Patent: \*Apr. 21, 2026**

(54) ULTRASONIC COMMUNICATION IN ADJUSTABLE IMPLANTS

(71) Applicant: Nuvasive Specialized Orthopedics, Inc., San Diego, CA (US)

(72) Inventors: Jorge Lopez Camacho, Aliso Viejo, CA (US); Shanbao Cheng, Aliso Viejo, CA (US); Youngsam Bae, Aliso Viejo, CA (US); Shawn Placie, Aliso Viejo, CA (US); Michael Moeller, Aliso Viejo, CA (US)

(73) Assignee: Globus Medical, Inc., Audubon, PA (US)

( \* ) Notice: Subject to any disclaimer, the term of this patent is extended or adjusted under 35 U.S.C. 154(b) by 831 days.

This patent is subject to a terminal disclaimer.

(21) Appl. No.: 17/361,726

(22) Filed: Jun. 29, 2021

(65) Prior Publication Data

US 2022/0015811 A1 Jan. 20, 2022

Related U.S. Application Data

(60) Provisional application No. 63/051,894, filed on Jul. 15, 2020.

(51) Int. Cl.
*A61B 17/72* (2006.01)
*A61B 17/80* (2006.01)
(Continued)

(52) U.S. Cl.
CPC *A61B 17/8004* (2013.01); *A61B 2017/00221* (2013.01); *A61B 2017/00411* (2013.01);
(Continued)

(58) Field of Classification Search
CPC ............ A61B 17/7011; A61B 17/7014; A61B 17/7216; A61B 2017/681;
(Continued)

(56) References Cited

U.S. PATENT DOCUMENTS 2,702,031 A 2/1955 Wenger
3,111,945 A 11/1963 Von Solbrig
(Continued)

FOREIGN PATENT DOCUMENTS

CN 1697630 A 11/2005
CN 101040807 A 9/2007
(Continued)

OTHER PUBLICATIONS

Abe et al., "Experimental external fixation combined with percutaneous discectomy in the management of scoliosis.", Spine, 1999, pp. 646-653, 24, No. 7.
(Continued)

*Primary Examiner* — Anu Ramana

(57) ABSTRACT

The present disclosure broadly provides applications of communication at ultrasound frequencies to establish transcutaneous data communication between medical devices located on and/or within a body of a patient, including inter alia: features for adjustable implants including data communication, hermetic containment, and torque amplification features.

17 Claims, 14 Drawing Sheets

(51) Int. Cl.
  *A61B 17/00*          (2006.01)
  *A61B 17/68*          (2006.01)
(52) U.S. Cl.
  CPC .............. *A61B 2017/00477* (2013.01); *A61B*
        *2017/00991* (2013.01); *A61B 2017/681*
                                 (2013.01)
(58) Field of Classification Search
  CPC ........... A61B 2017/00411; A61B 2017/00991;
                                 A61B 2017/00221
  See application file for complete search history.

(56)                References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |

(56)　　　　References Cited

U.S. PATENT DOCUMENTS

| | | | |
|---|---|---|---|
| 6,730,087 | B1 | 5/2004 | Butsch |
| 6,761,503 | B2 | 7/2004 | Breese |
| 6,769,499 | B2 | 8/2004 | Cargill et al. |
| 6,789,442 | B2 | 9/2004 | Forch |
| 6,796,984 | B2 | 9/2004 | Soubeiran |
| 6,802,844 | B2 | 10/2004 | Ferree |
| 6,809,434 | B1 | 10/2004 | Duncan et al. |
| 6,835,207 | B2 | 12/2004 | Zacouto et al. |
| 6,852,113 | B2 | 2/2005 | Nathanson et al. |
| 6,918,838 | B2 | 7/2005 | Schwarzler et al. |
| 6,918,910 | B2 | 7/2005 | Smith et al. |
| 6,921,400 | B2 | 7/2005 | Sohngen |
| 6,923,951 | B2 | 8/2005 | Contag et al. |
| 6,971,143 | B2 | 12/2005 | Domroese |
| 7,001,346 | B2 | 2/2006 | White |
| 7,008,425 | B2 | 3/2006 | Phillips |
| 7,011,658 | B2 | 3/2006 | Young |
| 7,029,472 | B1 | 4/2006 | Fortin |
| 7,029,475 | B2 | 4/2006 | Panjabi |
| 7,041,105 | B2 | 5/2006 | Michelson |
| 7,060,080 | B2 | 6/2006 | Bachmann |
| 7,063,706 | B2 | 6/2006 | Wittenstein |
| 7,105,029 | B2 | 9/2006 | Doubler et al. |
| 7,105,968 | B2 | 9/2006 | Nissen |
| 7,114,501 | B2 | 10/2006 | Johnson et al. |
| 7,115,129 | B2 | 10/2006 | Heggeness |
| 7,135,022 | B2 | 11/2006 | Kosashvili et al. |
| 7,160,312 | B2 | 1/2007 | Saadat |
| 7,163,538 | B2 | 1/2007 | Altarac et al. |
| 7,189,005 | B2 | 3/2007 | Ward |
| 7,191,007 | B2 | 3/2007 | Desai et al. |
| 7,218,232 | B2 | 5/2007 | DiSilvestro et al. |
| 7,238,191 | B2 | 7/2007 | Bachmann |
| 7,241,300 | B2 | 7/2007 | Sharkawy et al. |
| 7,243,719 | B2 | 7/2007 | Baron et al. |
| 7,255,682 | B1 | 8/2007 | Bartol, Jr. et al. |
| 7,282,023 | B2 | 10/2007 | Frering |
| 7,285,087 | B2 | 10/2007 | Moaddeb et al. |
| 7,302,015 | B2 | 11/2007 | Kim et al. |
| 7,302,858 | B2 | 12/2007 | Walsh et al. |
| 7,314,443 | B2 | 1/2008 | Jordan et al. |
| 7,333,013 | B2 | 2/2008 | Berger |
| 7,357,037 | B2 | 4/2008 | Hnat et al. |
| 7,357,635 | B2 | 4/2008 | Belfor et al. |
| 7,360,542 | B2 | 4/2008 | Nelson et al. |
| 7,390,007 | B2 | 6/2008 | Helms et al. |
| 7,390,294 | B2 | 6/2008 | Hassler, Jr. |
| 7,402,134 | B2 | 7/2008 | Moaddeb et al. |
| 7,402,176 | B2 | 7/2008 | Malek |
| 7,429,259 | B2 | 9/2008 | Cadeddu et al. |
| 7,445,010 | B2 | 11/2008 | Kugler et al. |
| 7,458,981 | B2 | 12/2008 | Fielding et al. |
| 7,485,149 | B1 | 2/2009 | White |
| 7,489,495 | B2 | 2/2009 | Stevenson |
| 7,530,981 | B2 | 5/2009 | Kutsenko |
| 7,531,002 | B2 | 5/2009 | Sutton et al. |
| 7,553,298 | B2 | 6/2009 | Hunt et al. |
| 7,561,916 | B2 | 7/2009 | Hunt et al. |
| 7,611,526 | B2 | 11/2009 | Carl et al. |
| 7,618,435 | B2 | 11/2009 | Opolski |
| 7,658,754 | B2 | 2/2010 | Zhang et al. |
| 7,666,184 | B2 | 2/2010 | Stauch |
| 7,666,210 | B2 | 2/2010 | Franck et al. |
| 7,678,136 | B2 | 3/2010 | Doubler et al. |
| 7,678,139 | B2 | 3/2010 | Garamszegi et al. |
| 7,708,737 | B2 | 5/2010 | Kraft et al. |
| 7,708,762 | B2 | 5/2010 | McCarthy et al. |
| 7,727,143 | B2 | 6/2010 | Birk et al. |
| 7,753,913 | B2 | 7/2010 | Szakelyhidi, Jr. et al. |
| 7,753,915 | B1 | 7/2010 | Eksler et al. |
| 7,762,998 | B2 | 7/2010 | Birk et al. |
| 7,763,080 | B2 | 7/2010 | Southworth |
| 7,766,855 | B2 | 8/2010 | Miethke |
| 7,775,215 | B2 | 8/2010 | Hassler, Jr. et al. |
| 7,776,068 | B2 | 8/2010 | Ainsworth et al. |
| 7,776,075 | B2 | 8/2010 | Bruneau et al. |
| 7,787,958 | B2 | 8/2010 | Stevenson |
| 7,794,476 | B2 | 9/2010 | Wisnewski |
| 7,811,328 | B2 | 10/2010 | Molz, IV et al. |
| 7,835,779 | B2 | 11/2010 | Anderson et al. |
| 7,837,691 | B2 | 11/2010 | Cordes et al. |
| 7,862,586 | B2 | 1/2011 | Malek |
| 7,867,235 | B2 | 1/2011 | Fell et al. |
| 7,875,033 | B2 | 1/2011 | Richter et al. |
| 7,901,381 | B2 | 3/2011 | Birk et al. |
| 7,909,852 | B2 | 3/2011 | Boomer et al. |
| 7,918,844 | B2 | 4/2011 | Byrum et al. |
| 7,938,841 | B2 | 5/2011 | Sharkawy et al. |
| 7,985,256 | B2 | 7/2011 | Grotz et al. |
| 7,988,709 | B2 | 8/2011 | Clark et al. |
| 8,002,809 | B2 | 8/2011 | Baynham |
| 8,011,308 | B2 | 9/2011 | Picchio |
| 8,034,080 | B2 | 10/2011 | Malandain et al. |
| 8,043,299 | B2 | 10/2011 | Conway |
| 8,043,338 | B2 | 10/2011 | Dant |
| 8,057,473 | B2 | 11/2011 | Orsak et al. |
| 8,057,513 | B2 | 11/2011 | Kohm et al. |
| 8,083,741 | B2 | 12/2011 | Morgan et al. |
| 8,092,499 | B1 | 1/2012 | Roth |
| 8,095,317 | B2 | 1/2012 | Ekseth et al. |
| 8,105,360 | B1 | 1/2012 | Connor |
| 8,114,158 | B2 | 2/2012 | Carl et al. |
| 8,123,805 | B2 | 2/2012 | Makower et al. |
| 8,133,280 | B2 | 3/2012 | Voellmicke et al. |
| 8,147,549 | B2 | 4/2012 | Metcalf, Jr. et al. |
| 8,162,897 | B2 | 4/2012 | Byrum |
| 8,162,979 | B2 | 4/2012 | Sachs et al. |
| 8,177,789 | B2 | 5/2012 | Magill et al. |
| 8,197,490 | B2 | 6/2012 | Pool et al. |
| 8,211,149 | B2 | 7/2012 | Justis |
| 8,211,151 | B2 | 7/2012 | Schwab et al. |
| 8,221,420 | B2 | 7/2012 | Keller |
| 8,226,690 | B2 | 7/2012 | Altarac et al. |
| 8,236,002 | B2 | 8/2012 | Fortin et al. |
| 8,241,331 | B2 | 8/2012 | Arnin |
| 8,246,630 | B2 | 8/2012 | Manzi et al. |
| 8,252,063 | B2 | 8/2012 | Stauch |
| 8,267,969 | B2 | 9/2012 | Altarac et al. |
| 8,278,941 | B2 | 10/2012 | Kroh et al. |
| 8,282,671 | B2 | 10/2012 | Connor |
| 8,323,290 | B2 | 12/2012 | Metzger et al. |
| 8,357,182 | B2 | 1/2013 | Seme |
| 8,366,628 | B2 | 2/2013 | Denker et al. |
| 8,372,078 | B2 | 2/2013 | Collazo |
| 8,386,018 | B2 | 2/2013 | Stauch et al. |
| 8,394,124 | B2 | 3/2013 | Biyani |
| 8,403,958 | B2 | 3/2013 | Schwab |
| 8,414,584 | B2 | 4/2013 | Brigido |
| 8,425,608 | B2 | 4/2013 | Dewey et al. |
| 8,435,268 | B2 | 5/2013 | Thompson et al. |
| 8,439,926 | B2 | 5/2013 | Bojarski et al. |
| 8,444,693 | B2 | 5/2013 | Reiley |
| 8,469,908 | B2 | 6/2013 | Asfora |
| 8,470,004 | B2 | 6/2013 | Reiley |
| 8,486,070 | B2 | 7/2013 | Morgan et al. |
| 8,486,076 | B2 | 7/2013 | Chavarria et al. |
| 8,486,147 | B2 | 7/2013 | De Villiers et al. |
| 8,494,805 | B2 | 7/2013 | Roche et al. |
| 8,496,662 | B2 | 7/2013 | Novak et al. |
| 8,518,062 | B2 | 8/2013 | Cole et al. |
| 8,523,866 | B2 | 9/2013 | Sidebotham et al. |
| 8,529,474 | B2 | 9/2013 | Gupta et al. |
| 8,529,606 | B2 | 9/2013 | Alamin et al. |
| 8,529,607 | B2 | 9/2013 | Alamin et al. |
| 8,556,901 | B2 | 10/2013 | Anthony et al. |
| 8,556,911 | B2 | 10/2013 | Mehta et al. |
| 8,556,975 | B2 | 10/2013 | Ciupik et al. |
| 8,562,653 | B2 | 10/2013 | Alamin et al. |
| 8,568,457 | B2 | 10/2013 | Hunziker |
| 8,579,979 | B2 | 11/2013 | Edie et al. |
| 8,585,595 | B2 | 11/2013 | Heilman |
| 8,585,740 | B1 | 11/2013 | Ross et al. |
| 8,591,549 | B2 | 11/2013 | Lange |
| 8,591,553 | B2 | 11/2013 | Eisermann et al. |

(56)  References Cited

U.S. PATENT DOCUMENTS

| | | | |
|---|---|---|---|
| 8,613,758 B2 | 12/2013 | Linares |
| 8,617,220 B2 | 12/2013 | Skaggs |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,393,117 B2 | 7/2016 | Pool |
| 9,398,925 B2 | 7/2016 | Kiester |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |

(56) References Cited

U.S. PATENT DOCUMENTS

| | | |
|---|---|---|
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0250674 A1 | 9/2014 | Pool et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |
| 2017/0319858 A1* | 11/2017 | Radziemski ....... A61N 1/37223 |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| EP | 2915496 A1 | 9/2015 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |
| WO | 2017/066774 A1 | 4/2017 |
| WO | 2020/055874 A1 | 3/2020 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

(56) References Cited

OTHER PUBLICATIONS

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

Invis®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral malrotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

Korenkov et al., "Port function after laparoscopic adjustable gastric banding for morbid obesity.", Surgical Endoscopy, 2003, pp. 1068-1071, 17, No. 7.

Krieg et al., "Leg lengthening with a motorized nail in adolescents.", Clinical Orthopaedics and Related Research, 2008, pp. 189-197, 466, No. 1.

Kucukkaya et al., "The new intramedullary cable bone transport technique.", Journal of Orthopaedic Trauma, 2009, pp. 531-536, 23, No. 7.

Lechner et al., "In vivo band manometry: A new method in band adjustment", Obesity Surgery, 2005, p. 935, 15, No. 7.

Lechner et al., "Intra-band manometry for band adjustments: The basics", Obesity Surgery, 2006, pp. 417-418, 16, No. 4.

Li et al., "Bone transport over an intramedullary nail: A case report with histologic examination of the regenerated segment.", Injury, 1999, pp. 525-534, 30, No. 8.

Lonner, "Emerging minimally invasive technologies for the management of scoliosis.", Orthopedic Clinics of North America, 2007, pp. 431-440, 38, No. 3.

Matthews et al., "Magnetically adjustable intraocular lens.", Journal of Cataract and Refractive Surgery, 2003, pp. 2211-2216, 29, No. 11.

Micromotion, "Micro Drive Engineering•General catalogue.", 2009, pp. 14-24.

Mineiro et al., "Subcutaneous rodding for progressive spinal curvatures: Early results.", Journal of Pediatric Orthopaedics, 2002, pp. 290-295, 22, No. 3.

Moe et al., "Harrington instrumentation without fusion plus external orthotic support for the treatment of difficult curvature problems in young children.", Clinical Orthopaedics and Related Research, 1984, pp. 35-45, 185.

Montague et al., "Magnetic gear dynamics for servo control.", Melecon 2010-2010 15th IEEE Mediterranean Electrotechnical Conference, Valletta, 2010, pp. 1192-1197.

Montague et al., "Servo control of magnetic gears.", IEEE/ASME Transactions on Mechatronics, 2012, pp. 269-278, 17, No. 2.

Nachemson et al., "Intravital wireless telemetry of axial forces in Harrington distraction rods in patients with idiopathic scoliosis.", The Journal of Bone and Joint Surgery, 1971, pp. 445-465, 53, No. 3.

(56) References Cited

OTHER PUBLICATIONS

Nachlas et al., "The cure of experimental scoliosis by directed growth control.", The Journal of Bone and Joint Surgery, 1951, pp. 24-34, 33-A, No. 1.

Newton et al., "Fusionless scoliosis correction by anterolateral tethering . . . can it work?.", 39th Annual Scoliosis Research Society Meeting, 2004.

Oh et al., "Bone transport over an intramedullary nail for reconstruction of long bone defects in tibia.", Archives of Orthopaedic and Trauma Surgery, 2008, pp. 801-808, 128, No. 8.

Ozcivici et al., "Mechanical signals as anabolic agents in bone.", Nature Reviews Rheumatology, 2010, pp. 50-59, 6, No. 1.

Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.

Prontes, "Longest bone in body.", eHow.com, 2012.

Rathjen et al., "Clinical and radiographic results after implant removal in idiopathic scoliosis.", Spine, 2007, pp. 2184-2188, 32, No. 20.

Ren et al., "Laparoscopic adjustable gastric banding: Surgical technique", Journal of Laparoendoscopic & Advanced Surgical Techniques, 2003, pp. 257-263, 13, No. 4.

Reyes-Sanchez et al., "External fixation for dynamic correction of severe scoliosis", The Spine Journal, 2005, pp. 418-426, 5, No. 4.

Rinsky et al., "Segmental instrumentation without fusion in children with progressive scoliosis.", Journal of Pediatric Orthopedics, 1985, pp. 687-690, 5, No. 6.

Rode et al., "A simple way to adjust bands under radiologic control", Obesity Surgery, 2006, p. 418, 16, No. 4.

Schmerling et al., "Using the shape recovery of nitinol in the Harrington rod treatment of scoliosis.", Journal of Biomedical Materials Research, 1976, pp. 879-892, 10, No. 6.

Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.

Sharke, "The machinery of life", Mechanical Engineering Magazine, Feb. 2004, Printed from Internet site Oct. 24, 2007 http://www.memagazine.org/contents/current/features/moflife/moflife.html.

Shiha et al., "Ilizarov gradual correction of genu varum deformity in adults.", Acta Orthop Belg, 2009, pp. 784-791, 75, No. 6.

Simpson et al., "Femoral lengthening with the intramedullary skeletal kinetic distractor.", Journal of Bone and Joint Surgery, 2009, pp. 955-961, 91-B, No. 7.

Smith, "The use of growth-sparing instrumentation in pediatric spinal deformity.", Orthopedic Clinics of North America, 2007, pp. 547-552, 38, No. 4.

Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).

Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).

Stokes et al., "Reducing radiation exposure in early-onset scoliosis surgery patients: Novel use of ultrasonography to measure length-ening in magnetically-controlled growing rods. Prospective validation study and assessment of clinical algorithm", 20th International Meeting on Advanced Spine Techniques, Jul. 11, 2013. Vancouver, Canada. Scoliosis Research Society.

Sun et al., "Masticatory mechanics of a mandibular distraction osteogenesis site: Interfragmentary micromovement.", Bone, 2007, pp. 188-196, 41, No. 2.

Synthes Spine, "VEPTR II. Vertical Expandable Prosthetic Titanium Rib II: Technique Guide.", 2008, 40 pgs.

Synthes Spine, "VEPTR Vertical Expandable Prosthetic Titanium Rib, Patient Guide.", 2005, 26 pgs.

Takaso et al., "New remote-controlled growing-rod spinal instrumentation possibly applicable for scoliosis in young children.", Journal of Orthopaedic Science, 1998, pp. 336-340, 3, No. 6.

Teli et al., "Measurement of forces generated during distraction of growing rods.", Journal of Children's Orthopaedics, 2007, pp. 257-258, 1, No. 4.

Tello, "Harrington instrumentation without arthrodesis and consecutive distraction program for young children with severe spinal deformities: Experience and technical details.", The Orthopedic Clinics of North America, 1994, pp. 333-351, 25, No. 2.

Thaller et al., "Limb lengthening with fully implantable magnetically actuated mechanical nails (PHENIX®)—Preliminary results.", Injury, 2014 (E-published Oct. 28, 2013), pp. S60-S65, 45.

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

* cited by examiner

ULTRASONIC COMMUNICATION IN ADJUSTABLE IMPLANTS

CROSS REFERENCE TO RELATED APPLICATIONS

The present application claims the benefit of U.S. Provisional Application No. 63/051,894, filed Jul. 15, 2020, which is incorporated by reference as though fully set forth herein.

BACKGROUND

Field of Disclosure

The present disclosure pertains to the field of medical devices. More specifically, the present disclosure pertains to adjustable implants configured for ultrasonic communication.

Background

Medical implants have various forces exerted on them in vivo, especially medical implants that are adjustable in situ. Such adjustable medical implants, for example, may be used in limb lengthening and spinal corrective surgical procedures to treat conditions such as limb deformities and scoliosis. Typically, these adjustable medical implants are secured to one or more bones and gradually adjusted over time until some desired patient outcome is achieved.

These adjustable implants and procedures do not include an accurate and non-invasive means of measurement of in vivo conditions, such as forces and pressures, present at the implant site. Particularly, after the implant is implanted and during the course of treatment. What is needed are devices and methods to communicate needed measurements of conditions present at the implant site non-invasively.

Further, these adjustable implants and procedures do not include reliable transcutaneous communication devices or methods to achieve bidirectional communication of power/data between implants and other medical devices.

SUMMARY

In one aspect, the present disclosure provides an adjustable implant, the adjustable implant having an ultrasonic transducer, wherein the ultrasonic transducer is configured to one or more of: send and receive an ultrasonic signal. In some embodiments, the ultrasonic signal may be converted into one or more of power and electrical energy. In some embodiments, the ultrasonic signal may be modulated, for example, to include control instructions for the adjustable implant.

In one aspect, the present disclosure provides an adjustable implant including: an actuator and at least one ultrasonic transducer, wherein the adjustable implant is configured to receive an ultrasonic signal from an external transceiver and convert the ultrasonic signal into one or more of electrical energy and data.

In one aspect, the present disclosure provides an external transceiver configured to be placed adjacent to a patient's skin having at least one ultrasonic transducer, wherein the at least one ultrasonic transducer is configured to transmit an ultrasonic signal to an implant.

In one aspect, the present disclosure provides an adjustable implant including an actuator and at least one ultrasonic transducer, wherein the adjustable implant is configured to receive an ultrasonic signal from an external transceiver, and wherein the adjustable implant is configured for bidirectional and transcutaneous ultrasonic data communication with the external transceiver via the ultrasonic transducer. In some embodiments, the external transceiver is a device configured to be placed adjacent to the skin of a patient. In some embodiments, the external transceiver may include an external adjustment device. In some embodiments, the external transceiver is configured to control the actuator of the adjustable implant.

In one aspect, the present disclosure provides a system including an adjustable implant and an external transceiver, the adjustable implant having at least one ultrasonic transducer configured to receive an ultrasonic signal sent by the external transceiver and convert the ultrasonic signal into one or more of electrical energy and data.

In some aspects, the present disclosure provides methods of achieving one or more of transcutaneous data communication with and control of medical implants. In some embodiments, the medical implants may be disposed subcutaneously within a body of a patient.

BRIEF DESCRIPTION OF THE DRAWINGS

These and other features may be further understood by those with skill in the art upon a review of the appended drawings, wherein.

DETAILED DESCRIPTION

Figure 1:
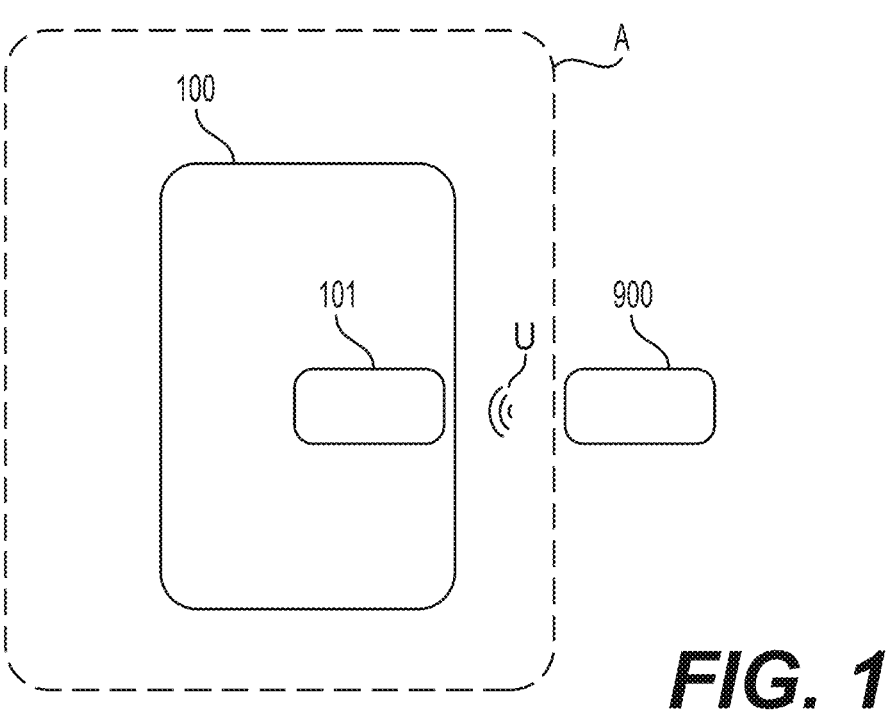
FIG. 1 shows an implant in accordance with a first embodiment, the implant located within a body of a patient and configured to communicate with an external transceiver.

For purposes of explanation and not limitation, details and descriptions of certain embodiments are hereinafter provided such that one having ordinary skill in the art may be enabled to practice the subject matter. These details and descriptions are representative only of certain embodiments, and a myriad of other embodiments which will not be expressly described will be readily understood by those having skill in the art upon a thorough review hereof. Accordingly, any reviewer of the instant disclosure should interpret the scope of this disclosure by the claims, and such scope shall not be limited by the embodiments described and illustrated herein.

Bidirectional ultrasonic communication in medical implants can provide power, enhanced control, and biofeedback between implants and other devices.

Information may be conveyed within the body of an organism, such as a human, in radio frequency (RF) signals, which utilize electromagnetic waves. However, RF signals experience large amounts of attenuation in aqueous tissues, bone tissues, and largely reflect off metallic surfaces. Ultrasound waves and ultrasound signals experience much less attenuation within the body. The ultrasound waves can convey information via known amplitude and phase shifting techniques. Phase-Shift Keying is a digital modulation process which conveys data by changing the phase of a constant frequency carrier wave. The modulation is accomplished by varying the sine and cosine inputs at a precise time. It is widely used for wireless LANs, RFID and BLUETOOTH (BT). Binary phase-shift keying (BPSK) or any modulation technique may be used in ultrasound communication including: On-Off Keying (OOK), Amplitude-Shift Keying (ASK) and Frequency-Shift Keying (FSK).

The frequency of ultrasound sound waves chosen to establish the bidirectional ultrasonic communication in implants may be in any frequency of ultrasound, and are generally greater than 20 kilohertz. In some embodiments, the frequency of ultrasound sound waves may be between 200 and 400 kilohertz, for example, about 300 kilohertz. Utilizing ultrasound sound waves for power and/or data transmission in medical implants may be beneficial in that (1) ultrasound sound waves have favorable propagation and less attenuation characteristics than RF through metal or solid mediums (e.g., metallic medical implants), and (2) ultrasound sound waves can transmit data transcutaneously through various aqueous tissues in animals (e.g., human skin, muscle and bone).

Once a bidirectional ultrasound communication link is established, the implant may have a power consumption of between 0.5 mW and 80 mW, 1 mW and 60 mW, and 2.0 mW and 40 mW, 10 mW, 5 mW, and any subrange thereof. The ultrasound transducer may consume about 20 mW of power when in operation. The transducer may be configured to transmit data through at least four inches of water or aqueous tissues at a rate of 5 values per second (1 kb/s) with a data reliability of 95%. Data reliability transmitted from the transducer at these power levels may be at least 95%, at least 98%, at least 99%, at least 99.9%, or 100%. "Data reliability" means reliability over 10 minutes as calculated from a bit error rate (BER).

FIG. 1 is a schematic diagram showing an implant 100 configured to receive wireless power via an ultrasound signal U. The implant 100 is shown disposed within a body of a patient A. The patient A may be any animal including a human. The implant 100 includes at least one ultrasonic transducer 101 configured to receive the ultrasonic signal U sent by an external transceiver 900, and convert that ultrasonic signal U to electrical energy. The ultrasonic transducer 101 may be, for example, a piezoelectric transducer, and the piezoelectric transducer may be operably connected to other circuitry within the implant 100. The electrical energy harvested by the ultrasonic transducer 101 may be used to activate and power any circuitry disposed within the implant 100. Similarly, the implant 100 may include a power storage device. For example: one or more of a battery, a capacitor, and similar components for storing electrical charge.

The implant 100 may be, by way of example, an adjustable implant, a distraction rod, an intramedullary rod, an expandable intervertebral cage, and any other medical device intended for placement one or more of: on and within the body of a patient. In some embodiments, wireless activation and or powering of the implant 100 using ultrasonic waves may eliminate a need for an internal power storage device in various types of medical implants.

The implant 100, may be made of, among other things, polyether ether ketone (PEEK), polyetherketone (PEK), titanium (Ti), BioDur, and any other material known and used to make implants, including any biocompatible thermoplastic and metallic materials. Preference may be given to materials with known favorable ultrasonic transmission characteristics. The implant may be fabricated using known fabrication techniques for the materials chosen including, for example, additive manufacturing, welding, bonding, and molding techniques. The implant may be dimensioned in accordance with a treatment plan. And the implant may be adjustable and may include other electronic components and circuitry to operably couple the ultrasonic transducer 101 to a controller.

The ultrasonic transducer 101 may include any device that induces sound waves or mechanical vibration in the ultrasound spectrum, including, for example, a piezoelectric transducer, a crystal ultrasonic transducer, a lead zirconate titanate (PZT) ultrasonic transducer, piezoelectric polyvinylidene fluoride (PVDF) ultrasonic transducer, capacitive micromachined ultrasonic transducers (CMUT), piezoelectric micromachined ultrasonic transducers (PMUT), and any ultrasonic transducer known and used.

In some embodiments, the external transceiver 900 may retrieve an ID tag of the implant 100 using an ultrasound signal U. The implant 100 may include an integrated circuit and an ultrasonic transducer 101, which are used to transmit data to the external transceiver 900 using an ultrasound signal. In some embodiments, the external transceiver may obtain an ID tag, in operation resembling RFID, by providing power to the implant 100 using an ultrasound signal wherein the implant 100 harvests enough energy from the ultrasound signal to enable the implant 100 to transmit the ID tag via an ultrasonic signal transmitted back to the external transceiver 900 by the ultrasonic transducer 101. In some embodiments, enough energy is harvested to activate the implant 100 and establish a bidirectional communication link between the implant 100 and the external transceiver 900 using ultrasound signals.

In some embodiments, an array containing a plurality of ultrasonic transducers may be provided to provide enhanced reception capabilities to the implant or external device 900. Particularly in patients that are overweight, it is advantageous to provide more than one ultrasonic transducer to improve transmission/reception of the ultrasonic signal U. For example, an array of ultrasonic transducers may be provided at the external transceiver 900 with the ultrasonic transducers focused at a focal distance equal to the distance from the array to the adjustable implant 100. The focal distance of the array may be fixed. In some embodiments, the ultrasonic transducers are placed on mechanical mounts to move each ultrasonic transducer independently to synchronously move the focal point of the array. In some embodiments, the array may include a phased array and the frequency at each transducer may be varied to move the focal point relative to the array.

Figure 2:
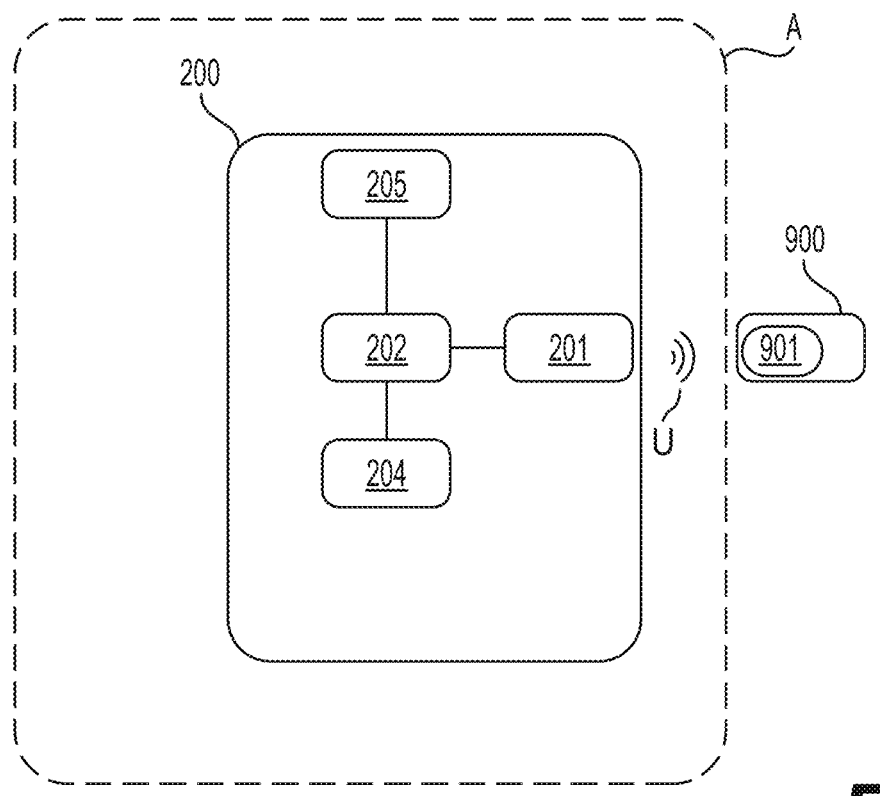
FIG. 2 shows an implant in accordance with a second embodiment, the implant located within a body of a patient and configured for transcutaneous bidirectional ultrasonic data communication.

Turning to FIG. 2, a schematic diagram is provided showing an implant 200 in accordance with a second embodiment, the implant 200 configured for transcutaneous ultrasonic data communication with at least an external transceiver 900. The implant 200 is shown having operatively connected circuitry including at least one ultrasonic transducer 201, a controller 202, a sensor 205, and a power storage device 204.

The controller 202 may be any type of controller 202 known and used in the art including: high performance microcontrollers (MCUs), Programmable System on Chip (PSoC), Application Specific Integrated Circuit (ASIC) and any other type of controller and microcomputer. The controller 202 may be disposed on a printed circuit board which may also contain other electronic circuitry and connect other electrical components including: Analog to Digital Converter (ADC), Digital to Analog Converter (DAC), op-amps, memory, phase shifters, and any other electrical component. The controller may further include a frequency synthesizer (i.e., creates carrier waves for ultrasonic transducer 201), power amplifiers and noise filters (i.e., conditions carrier wave), power and read strain gauge (i.e., force sensor controls), and may be configured to adjust carrier waves, power, etc., such as by computer executable instructions. In some embodiments, the computer executable instructions may interface with a user via a graphical user interface.

An energy storage device 204 is provided. The energy storage device 204 may include a battery, a capacitor, and any other electronic charge or power storage device. The energy storage device 204 may include a rechargeable battery (e.g., Lithium ion rechargeable battery). The power storage device 204 may include a solid state battery and any battery having any known mechanism or battery chemistry. Compliance with national/regional regulatory bodies may play a part in choosing an optimal power storage device for medical implants.

The implant 200 may include a charging circuit operably connected to the power storage device 204 and the piezoelectric transducer 201. The charging circuit may be integrated into one or more of the controller 202 and the printed circuit board. The charging circuit may include a digital switch wherein, upon receiving an ultrasonic signal modulated at a first activation frequency, the electronic switch is configured to enable charging of the power storage device with electrical energy harvested by the ultrasonic transducer. The power storage device 204 may be operably connected to the controller 202 via any electronic conductor including wires, boards, and interconnects.

In other embodiments, other known wireless charging circuits and techniques, including inductive coupling and magnetic coupling, may be used to wirelessly transfer power to the implant 200.

In some embodiments, an external transceiver 900 may activate the circuitry of the implant 200 by transmitting an ultrasound signal to the ultrasonic transducer 201. The ultrasound signal may be received by the ultrasonic transducer 201 and converted into electrical energy. The controller 202 may be programmed such that, upon receipt of an ultrasound signal corresponding to a particular modulated signal, for example a particular step function of a particular temperance, the controller 202 will open/close an electrical switch and activate the device and place the implant 200 in an active and awake state. Similarly, in other embodiments, a particular step function may be used to open/close the electrical switch to deactivate the device from the awake state to conserve power of the power storage device 204.

In some embodiments, the controller 202 may be programmed to time out after a certain period of time, for example if the piezoelectric transducer 201 has not sent or received ultrasonic signals for a set period of time.

In some embodiments, the controller 202 may be programmed to turn off the power storage device 204 and to put the implant 200 to sleep for a certain period of time to conserve power. For example, the controller may activate the implant 200 to transmit ultrasonic signal with 25% duty cycle. Between the pulse width, the second the implant 200 is said to be active or in awake state. The controller may deactivate the implant 200 during the rest of the period. This state is said to be deactivated or in a sleep state.

In some embodiments, the implant 200 may include one or more sensors 205 operably connected to the controller 202. The sensors 205 may be designed to measure temperature, force, pressure, capacitance, resistance, and any other physical property or characteristic of the implant 200 or measure information indicative of a biological condition from surrounding anatomical structures of the patient A. The sensor 205 may include, for example, a position sensor, an optical sensor, a force sensor, and any known sensor. In the instant embodiment, the sensor 205 may be configured to sense force, for example.

In some embodiments, the sensor 205 may include a Micro-Electro-Mechanical-System (MEMS) sensor. These sensors provide a reduced profile (e.g. 1 μm-100 μm size). The MEMS sensor may include an accelerometer, pressure sensor, gas sensors, humidity sensor, a gyrosensor, ambient light sensor, optical sensor, gesture sensor, proximity sensor, touch sensor, or any other mechanical element or sensory functionality.

The sensor 205 may communicate a sensor reading to the controller 202, which may convert the reading to a modulated electrical signal. The modulated electrical signal may then be used to drive the ultrasonic transducer 201, which then transmits an ultrasonic signal U at a frequency corresponding to the modulated electrical signal.

The controller 202 may change analogue information from the sensor 205 to digital values and may drive modulation of the ultrasonic transducer 201, to transmit data using modulated ultrasound waves.

The implant 200 may be any type of implant including an adjustable implant. The adjustable implant may include an actuator. As one with skill in the art may appreciate, the implant may be configured to harvest ultrasonic waves transmitted by another medical device, and convert the ultrasonic waves to electrical energy to power the actuator. In some embodiments, closed loop control of the implant 200 may be achieved using the ultrasound signal to relay information between the implant 200 and the external transceiver 900.

In some embodiments, the actuator may include one or more of a rotatable magnet, an electric motor, a piezoelectric motor, and any type of actuator known and used in the art. In some embodiments, where the actuator includes a rotatable magnet, the controller may be configured to communicate, for example, an adjustment length of the adjustable implant, a number of rotations of the rotatable magnet, a magnetic field strength at the routable magnet, and any information corresponding to the adjustable implant. In embodiments where the actuator includes a motor, the controller may be configured to communicate at least, for example, one or more of: an adjustment length of the adjustable implant, adjustment instructions for the motor, closed loop control of the motor, and any information corresponding to the adjustable implant.

Ultrasonic communication provides a reliable communication link between one or more implants in or near the body, one or more external transceivers, and one or more tertiary devices. An ultrasonic signal can even be used to establish a network of devices placed on or within the body of a patient.

The implant 200 may include any type of adjustable implant. By way of example, the adjustable implant 200 may include magnetically adjustable systems, such as the PRECICE® or MAGEC® magnetically adjustable implant systems for spinal and limb lengthening procedures sold by NuVasive, Inc. of San Diego, California. Such adjustable systems are disclosed in, for example, U.S. Pat. Nos. 9,398, 925 and 9,393,117, which are incorporated by reference herein in their entireties.

The actuator of these embodiments may include a magnet connected to a lead screw. Upon an axial rotation of the magnet by an externally applied rotating magnetic field, the lead screw will rotate. Rotation of the lead screw will cause an axial distraction of the adjustable implant, and thereby change a dimension of the adjustable implant. Rotation of the magnet may be achieved using an external adjustment device including one or more external magnets and which may further include one or more of an external transceiver and an external adjustment device configured for ultrasonic communication.

Implants experience numerous forces in vivo. For example, as the above mentioned adjustable implant is distracted, axial forces will push down on the magnet. Thrust bearings are provided to mitigate the effect of these forces on the rotation of the magnet. The thrust bearings transfer the axial load from the lead screw to the housing of the adjustable implant, diverting the axial forces away from the magnet and onto the housing.

Figure 3:
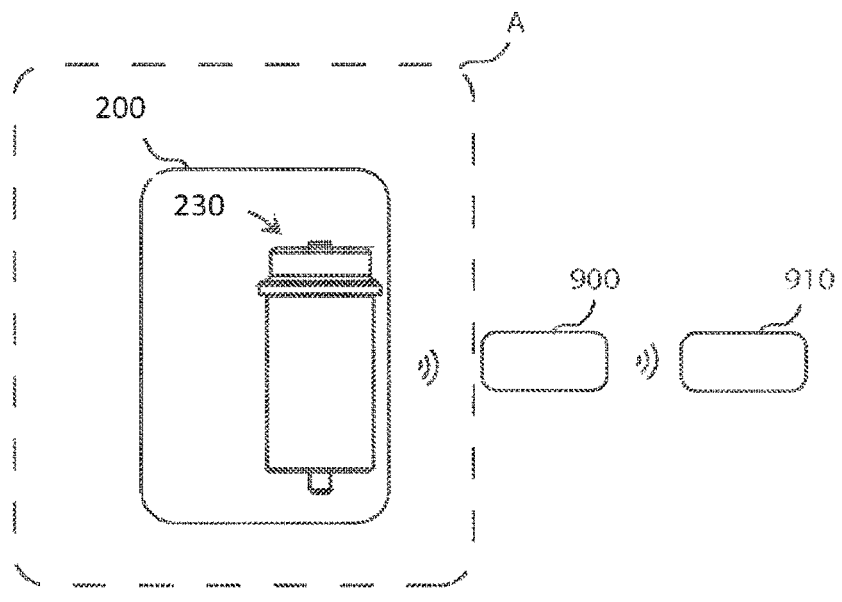
FIG. 3 shows a sensor module coupled to an implant and disposed within the body of a patient, the sensor module enabling the implant with ultrasound data communication.

Turning to FIG. 3, an implant 200 in accordance with the second embodiment is shown including a sensor module 230 disposed therein. The sensor module 230 includes an ultrasonic transducer 201 including, for example, a tubular piezoelectric transducer operably connected to one or more of a controller 202, a power storage device 204, and a sensor 205. The ultrasonic transducer 201 is configured to transmit and receive ultrasonic signals, convert the ultrasonic waves of the ultrasonic signals into electrical energy, and communicate that electrical energy to one or more of: the controller 202 for data communication and the power storage device 204 for charging the power storage device 204. As discussed above, the controller 202 may include any type of controller

202 known and used in the art, including high performance microcontrollers (MCUs), Programmable System on Chip (PSoC), and any other type of controller or microcomputer. The controller 202 may be disposed on a printed circuit board which may also contain other electronic circuitry and components therein including: Analog to Digital Converter (ADC), Digital to Analog Converter (DAC), op-amps, memory and any other electronic circuitry known and used in the art.

As discussed above, the power storage device 204 may include a battery, a capacitor, and any other rechargeable power storage device.

The sensor module 230 may include a recharging circuit operably connected to the energy storage device 204 and the ultrasonic transducer 201. The recharging circuit may be one or more of: integrated into the controller 202 and disposed on another printed circuit board.

The sensor module 230 is configured to communicate one or more of power and data with the external transceiver 900. The external transceiver may include an external adjustment device or remote control configured to command the adjustable implant 200. In some embodiments, the sensor module 230 is configured to transmit information relating to one or more of a biological condition of the patient A and information relating to the implant. The information relating to the implant may include one or more of a reading from the sensor 205, a dimension of the implant, and any other information useful to a surgeon or patient.

In some embodiments, an external transceiver 900 may activate the circuitry of the sensor module 230 by transmitting an ultrasonic signal to the sensor module 230. The ultrasound waves are received by the ultrasonic transducer 201 and converted into electrical energy. The controller 202 may be programmed such that, upon receipt of ultrasonic waves corresponding to a particular modulated signal, for example a particular step function of a particular temperance, the controller 202 may open/close an electrical switch and activate the sensor module 230. Similarly, a second particular step function may open/close the electrical switch and deactivate the sensor module 230 to conserve energy.

In some embodiments, the controller 202 may be programmed to time out after a certain period of time, wherein if, for example, the ultrasonic transducer 201 has not sent or received ultrasonic waves for a test period of time, the sensor module 230 will change its state into hibernation mode to thereby conserve charged power levels of the energy storage device 204, extending a battery life thereof.

In some embodiments, the sensor module 230 may be configured to have a power consumption of between 0.5 mW and 80 mW. The ultrasonic transducer 201 may consume about 20 mW of power when in operation. The ultrasonic transducer 201 may be configured to transmit data at least four inches through water and aqueous tissue at a rate of 5 values per second (1 kb/s) with a data reliability of 95%. Data reliability transmitted from the ultrasonic transducer 201 at these power levels may be at least 95%, at least 98%, at least 99%, at least 99.9%, or 100%. "Data reliability" is based on errors measured over 10 minutes as calculated from a bit error rate (BER).

In some embodiments, the sensor module 230 may include one or more sensors 205 operably connected to the controller 202. The sensors 205 may be designed to measure force, temperature, pressure, capacitance, resistance, and be any other type of sensor commonly known and used in the art.

In some embodiments, the sensor 205 is configured to communicate a sensor reading to the controller 202, which may convert the reading to one or more of a digital and analog modulated electrical signal. The modulated electrical signal may then be used to drive the ultrasonic transducer 201, which then transmits ultrasound waves transcutaneously. These ultrasound waves are observable to one or more of an external transceiver 900, a tertiary device 910, and/or other implants configured for ultrasound communication. In some embodiments, forms of modulation may include: on-off keying, amplitude shift keying (ASK), frequency shift keying (FSK), phase shift keying (PSK), analogue frequency modulation, and any other form of modulation commonly known and used for data transmission. Advantageously, signals that are modulated may consume less power than non-modulated signals and may be transmitted and received at greater distance from the sensor module 230 than non-modulated signals. Modulated signals may also have a greater accuracy than non-modulated signals.

In some embodiments, the sensor module 230 includes an encapsulation providing a hermetic seal to the sensor module 230. In order to prevent air gaps or pockets of unnecessary ultrasonic impedance, in some embodiments, the ultrasonic transducer 201 is coupled to at least a portion of the encapsulation using one or more of a conductive epoxy and/or a liquid gel. In this embodiment, the sensor module 230 is disposed adjacent to a surface of the adjustable implant 200 to minimize air-gaps, reflection, and impedance of ultrasound signals reaching the ultrasonic transducer 201.

The conductive epoxy may include any conductive material to reduce air gaps, including aluminum epoxy, copper epoxy, copper tape, Ti-epoxy, industry acoustic couplant, and any other material providing favorable electrical and/or acoustic conductive properties. In some embodiments, gels and liquid gels are used. When selecting a conductive epoxy, one may consider: (i) impedance matching to improve the ultrasonic transmission efficiency between the adjustable implant and the ultrasonic transducer, and (ii) the circuit grounding the electronics.

In the instant embodiment, the adjustable implant 200 includes a sensor module 230 forming an independent package configured to be integrated with and removed from various medical devices and implants, the sensor module 230 having various components and features. In some embodiments, these various components and features may be incorporated directly into the implant similar to those discussed in the schematic supra. This disclosure is intended to pertain to all variants.

In some embodiments, the sensor module 230 may be integrated with a processor circuit of an implant using any known type of intercommunication including: interconnects, cables and RF communication protocol. The sensor module 230 may receive data from the processor circuit of the implant directly, and communicate data transcutaneously to an external transceiver 900.

In some embodiments, the external transceiver 900 may obtain data directly from the implant, in the instant embodiment, data is obtained via the sensor module 230. The external transceiver 900 may then report the data to a tertiary device 910 using one or more of: an ultrasound communication connection, a cable connection, an RF data connection, a wifi connection, a BLUETOOTH(BT) connection, and any other data communication connection and protocol. The tertiary device 910 may include one or more of a computer, a cell phone, a server, the internet, and any other device. The tertiary device 910 may be enabled to drive the external transceiver 900 remotely to at least one of activate, communicate with, and control the adjustable implant 200 remotely, for example, across an internet connection.

The sensor module 230 enables the implant with ultrasound data communication. The sensor module 230 may enable any implant to transcutaneously transmit to and receive data from an external transceiver 900. The data may pertain to measurements obtained by the sensor module 230, corresponding to some physical property of the implant 200, or to some physical property of an anatomical item, tissue or structure of the body of the patient A.

Figure 4:
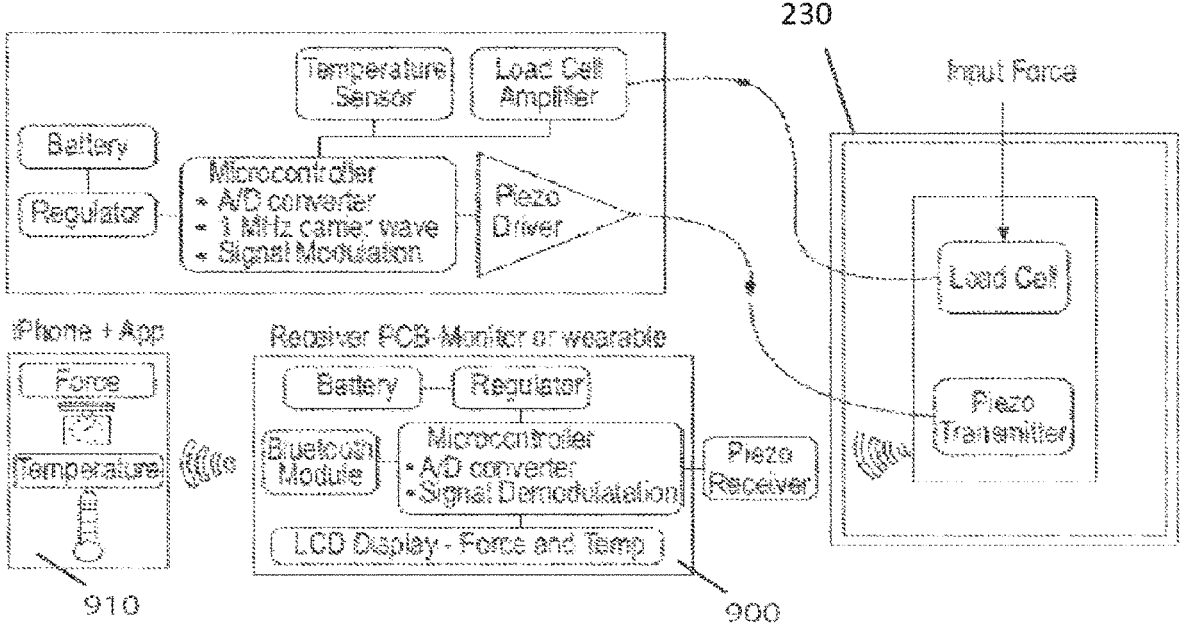
FIG. 4 shows a schematic of ultrasonic communication between an adjustable implant having a sensor module and an external transceiver.
Figure 4:
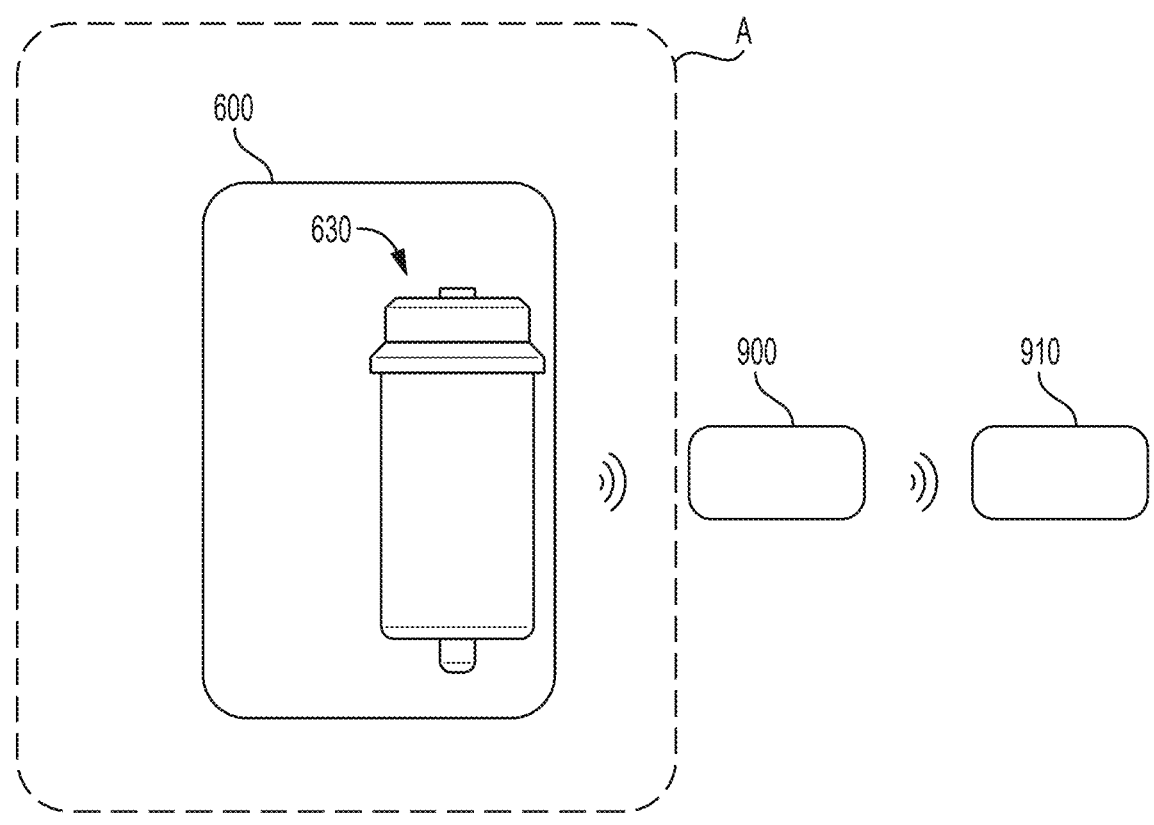

FIG. 4 shows an exemplary schematic of ultrasonic communication between a sensor module 230, an external transceiver 900, and a tertiary device 910. In the instant embodiment, the transceiver 900 may be a piece of wearable technology including a printed circuit board (PCB) receiver/transceiver module, and the tertiary device 910 may be a handheld device such as, for example, a mobile phone.

As discussed above, ultrasound data communication provides a reliable transcutaneous communication link between one or more implants and medical devices disposed in and near the body of a patient. Ultrasonic signals can be used to establish a network of devices placed on or within the body of a patient.

In some embodiments, the external transceiver 900 may include an external adjustment device configured for adjusting an adjustable implant. The external adjustment device may include one or more ultrasonic transducers disposed on a surface of the external adjustment device. Upon placing the external adjustment device in close proximity to a patient's skin, an ultrasonic communication link or network may be established between the external adjustment device and one or more implants configured for ultrasonic communication. The ultrasonic communication link is established to pass distraction information and bio-information between the external transceiver 900 and the one or more implants.

In some embodiments, the external transceiver 900 may be a wearable device. The wearable device may be, for example, a bracelet, a watch, an arm band, arm sleeve, arm brace, a leg band, a leg sleeve, a leg brace, a back brace, a body sleeve, a neck brace, a head brace, and any type of other wearable device known and used in the art. The wearable device may be cloth, plastic, metal, and may be made using additive manufacturing techniques, including 3D printing.

In some embodiments, the external transceiver may include an external adjustment device configured to adjust an adjustable implant.

The external transceiver may include an ultrasonic transducer, or multiple ultrasonic transducers forming one or more arrays. A one dimensional array has multiple ultrasonic transducers disposed in a column. Each ultrasonic transducer of a one dimensional array can be assigned a position relative to their position on the array. A two dimensional array has multiple ultrasonic transducers disposed in a matrix or pattern. Each ultrasonic transducer can be assigned a location relative to two dimensions of the matrix. Each array may be a focal array with two or more of the ultrasonic transducers directed to a focal point.

FIGS. 5A-5D illustrate an adjustable implant 300 in accordance with a third embodiment, the adjustable implant 300 configured for bi-directional ultrasonic communication. The adjustable implant 300 includes an actuator operatively coupled to an ultrasonic transducer configured for transcutaneous bidirectional ultrasonic data communication. The adjustable implant 300 is configured to be controlled by an external transceiver 900 and configured to send and receive ultrasound signals.

Figure 5:
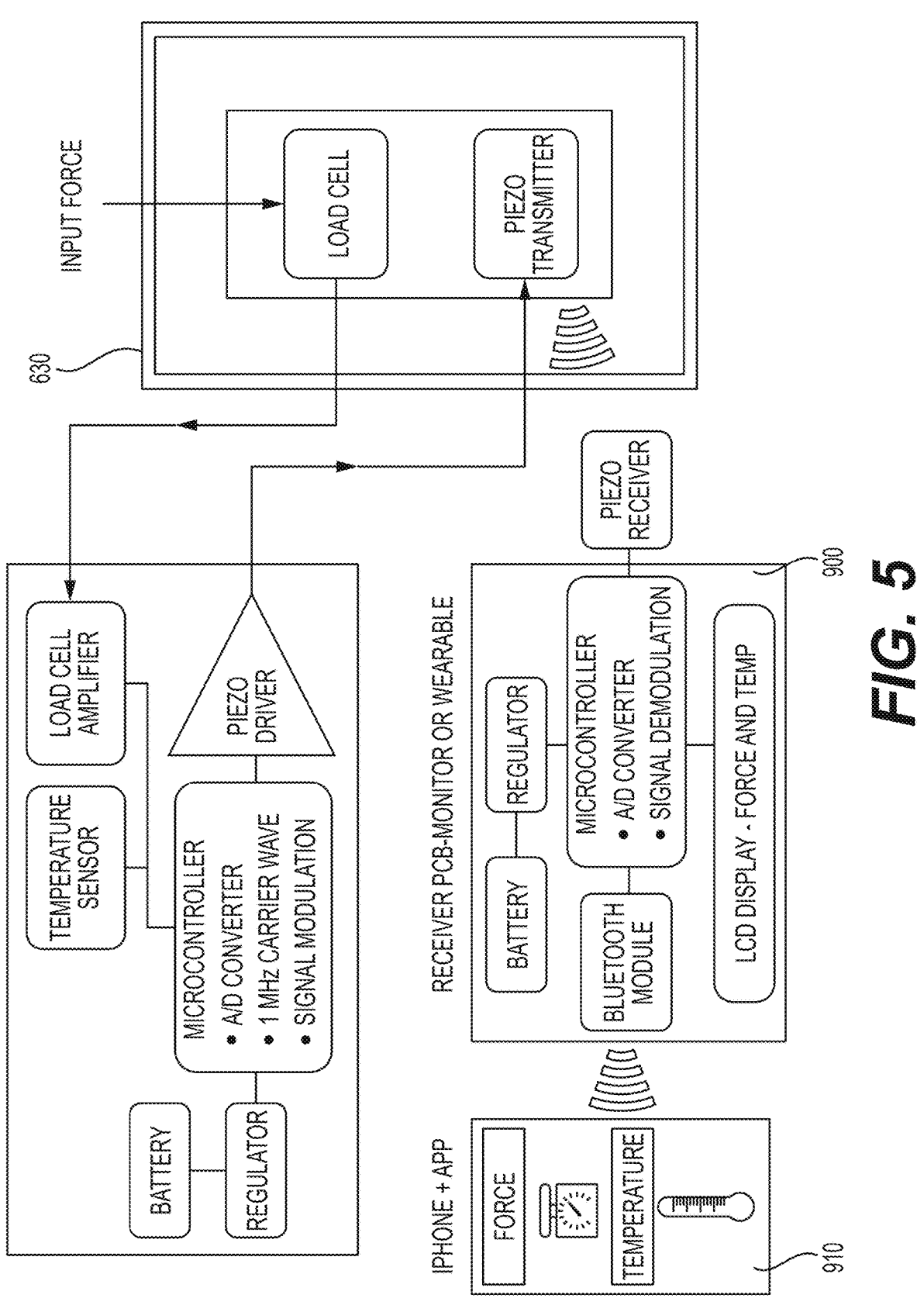
FIG. 5A shows a side view of an adjustable implant in accordance with a third embodiment, the adjustable implant shown in a first retracted configuration.
FIG. 5B shows a side view of the adjustable implant in accordance with the third embodiment, the adjustable implant shown in a second expanded configuration.
FIG. 5C shows a cross-sectional side view of the adjustable implant in accordance with the third embodiment, with an enhanced portion of the adjustable implant provided for convenience.
FIG. 5D shows an exploded view of the adjustable implant, illustrating some of the interior components of the adjustable implant in accordance with the third embodiment.
Figures 5A, 5B:
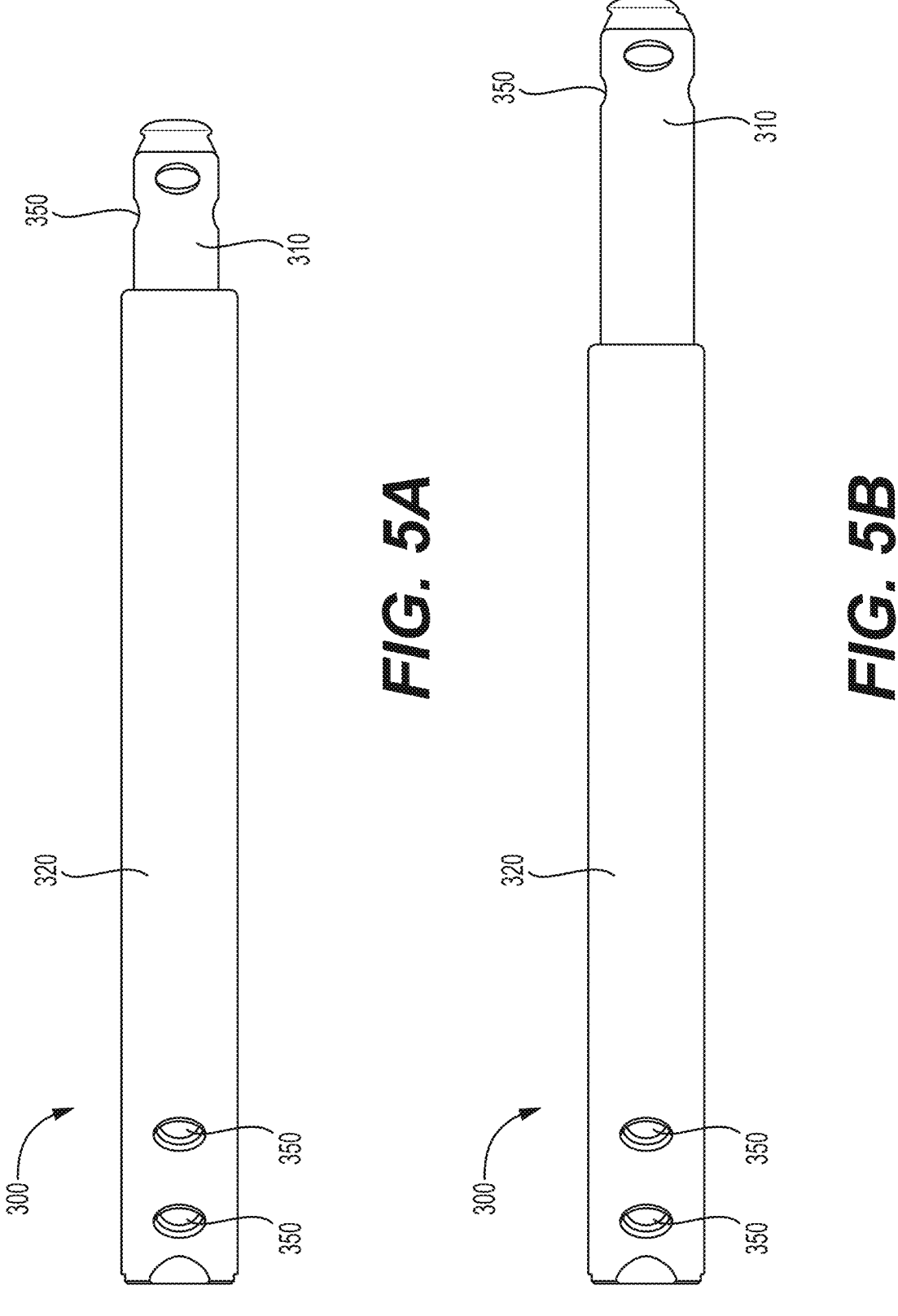

FIG. 5A shows a side view of the adjustable implant 300 in a first retracted configuration with at least a portion of a rod 310 telescopically received within an outer housing 320. In this embodiment, the adjustable implant 300 is an intramedullary rod configured to treat a bone of a patient. The rod 310 is configured to be telescopically received in and displaced from the outer housing 320 by the actuator. In some embodiments, this adjustable implant 300 may be configured to treat another skeletal deformity, for example, a distraction rod configured to be mounted to a plurality of vertebrae and configured to treat scoliosis.

In this embodiment, the outer housing 320 and the rod 310 include apertures 350 dimensioned to receive bone fixation devices there through, with the bone fixation devices configured to secure the implant 300 to a bone of a patient. The bone fixation devices may include bone screws, hooks, pins, rods, and any device known and used to secure an implant with respect to a patient's skeletal structure.

FIG. 5B shows a side view of the adjustable implant 300 in a second distracted configuration with the rod 310 shown telescopically displaced from the outer housing 320.

Figure 5C:
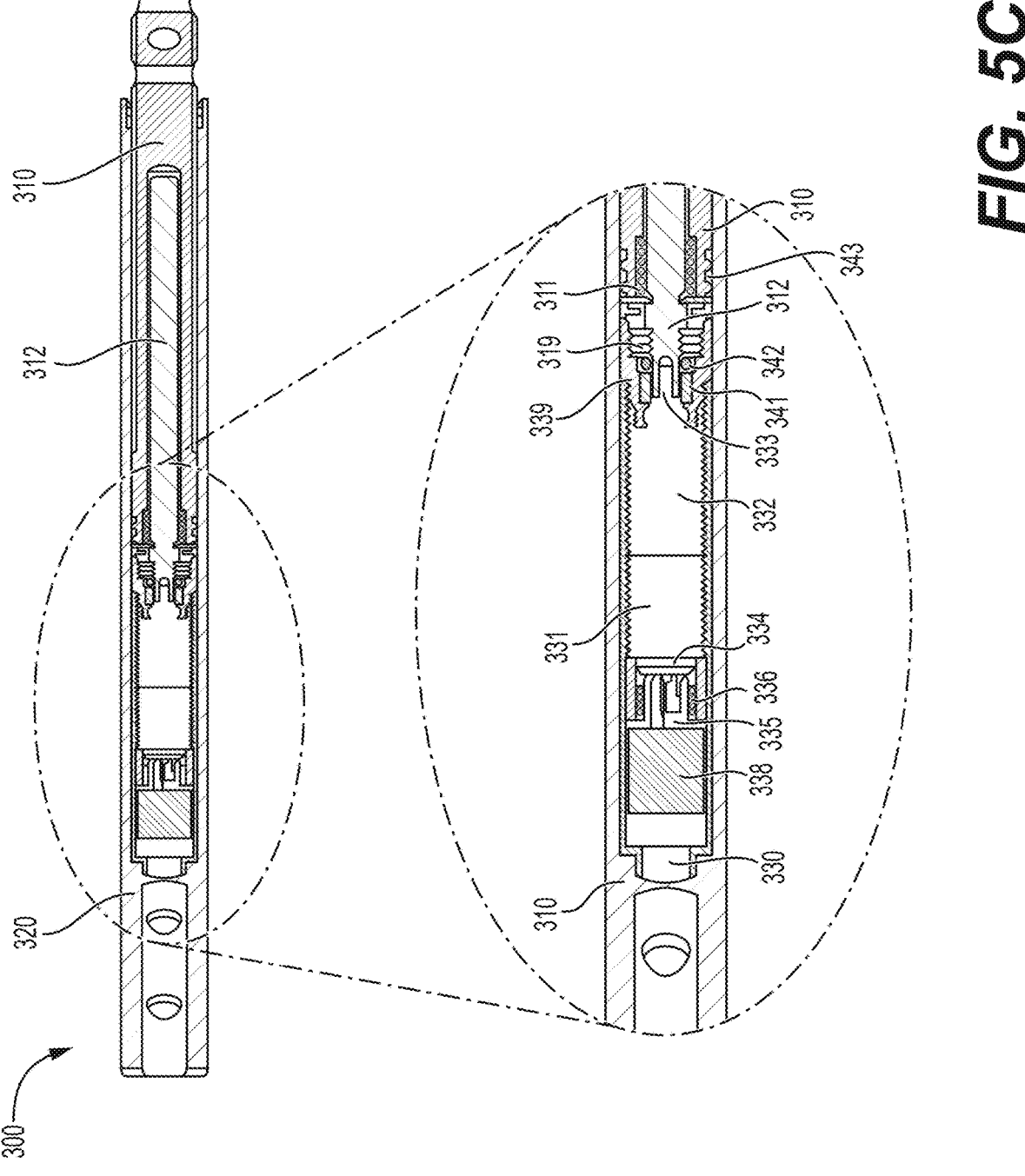

FIG. 5C shows a cross-sectional side view of the adjustable implant 300 along with an enhanced view of some of the interior components of the adjustable implant 300. In this embodiment, the rod 310 includes a cavity having an at least partially threaded interior surface configured to communicate with a lead screw 312. The at least partially threaded interior surface may include a thread disposed directly on an interior surface of the rod 310. In this embodiment, a threaded insert 311 is secured to the interior of the rod 310 by, for example, an epoxy. The threaded insert 311 may include a material different than the rod 310. In some embodiments, the threaded insert 311 may be made of a thermoplastic, e.g., polyether ether ketone (PEEK), polyether ketone (PEK), and/or a biocompatible metal such as titanium. Using a material for the threaded insert 311 that is softer than the lead screw 312 helps prevent binding and improves efficiency of the actuator.

The lead screw 312 is configured to rotate and displace the rod 310 relative to outer housing 320 upon a rotation of the lead screw 312 by an actuator. As one with skill in the art may appreciate, depending upon the direction of rotation of the lead screw 312, the lead screw 312 may move the rod 310 into or out of the outer housing 320.

The adjustable implant 300 includes an actuator. In this embodiment, the actuator is an electric motor 331. The electric motor 331 is operably connected to a gear housing 332 which may include one or more planetary gear sets configured to transfer rotational motion from the output of the electric motor 331 to the lead screw 312.

The electric motor 331 is operably coupled to a controller 334. The controller 334 is also operably coupled to an ultrasonic transducer 336 and a power storage device 338. The ultrasonic transducer 336 in this embodiment includes a hollow cylindrical ultrasonic transducer 336 configured to contact a periphery of the adjustable implant 300. The controller 334 may include a printed circuit board and may be configured for integration in a stacked configuration relative to the ultrasonic transducer 336 and the power storage device 338, with the electrical connections being established through a chassis 335 via interconnects 337.

The power storage device 338 and the electric motor 331 may be sealed within the adjustable implant 300 and additionally within a container 330 by a cap 339. The cap 339 may include threads configured to communicate with a threaded interior surface of the container 330 to seal the internal components therein. The cap 339 may include an aperture dimensioned to receive at least a portion of an output pinion 333 of one or more of the electric motor 331 and gear housing 332 therethrough, connecting one or more of the electric motor 331 and the gear housing 332 disposed within the container 330 to the lead screw 312 located outside of the container 330 and cap 339 subassembly, with the internal contents secured therein.

The cap 339 may include one or more of: a thrust bearing 319, a retainer capture sleeve 341 and a two-piece primary tension retainer 342, each configured to reduce an amount of axial load on the electronic motor 331 and the gear housing 332. The cap 339 may be designed to include a first aperture dimensioned to receive at least a portion of the gear housing 332, the output pinion 333, and the lead screw 312 therethrough. The cap 339 may include a second aperture dimensioned to receive the retainer capture sleeve 341 and the two-piece primary tension retainer 342. And additionally, the cap 339 may be designed to be integrated with a low friction bi-directional seal assembly 344 including at least one snap ring 345. These features divert axial load from the actuator to the container 330 and housing 320.

The encapsulated components of the container 330 and cap 339 assembly are disposed within a hollow interior cavity of the outer housing 320. As discussed above, the interior components of the container 330 are sealed therein by the cap 339. In this embodiment, additional layers of encapsulation are provided by: at least one O-ring 343 disposed between the outer housing 320 and the rod 310 and a low friction bi-directional seal assembly 344 including the two snap rings 345. In some embodiments, a second cap may be disposed at the end of the outer housing 320 sealing the hollow interior cavity of the outer housing 320.

As one with skill in the art may appreciate, in some embodiments, the adjustable implant 300 may include any and all the various ultrasonic communication features and capabilities as further described throughout this disclosure. For example, one or more of the electric motor 331 and the controller 334 may be configured to send and receive data via ultrasonic communication using the ultrasonic transducer 336. In some embodiments, the data may include adjustment instructions for the actuator. In some embodiments, the adjustment instructions include active closed loop control of the actuator. Additionally, in some embodiments, the data transmitted across the ultrasonic communication link may be related to the patient including, for example, data corresponding to a biological condition.

A benefit of using an electronic motor 331 to drive the adjustable implant 300 includes being able to monitor current draw of the electric motor 331 to determine an amount of force applied by the adjustable implant 300. In this embodiment, the controller 334 may monitor the current draw of the electric motor 331 and determine an amount of force applied to the bone of the patient. Similar to FIG. 2, the controller 334 may communicate the amount of force to an external transceiver 900 using the ultrasonic transducer 336. And the external transceiver 900 and/or a tertiary device 910 may use this information to calculate new distraction instructions for the adjustable implant 300 and communicate the new distraction instructions to the adjustable implant 300 using an ultrasonic signal.

In some embodiments, the lead screw 312 may include a thread pitch chosen and configured to minimize an amount of energy consumed by the electric motor 331 to move the rod 310 relative to the outer housing 320. In some embodiments, the pitch of the lead screw 312 may be chosen to optimize efficiency of the electric motor 331. Efficiency determines an amount of power consumption and indirectly defines a size of the power storage device 338. Maximizing lead screw 312 efficiency minimizes power consumption and enabling use of a smaller power storage device 338. Thereby, minimizing a size of the adjustable implant 300. In this embodiment, a lead screw pitch of 20 threads per inch (tpi) is chosen for the small diameter lead screw 312. A lead screw pitch of 20 tpi is four times more efficient than, for example, a lead screw pitch of 80 tpi. The pitch of the lead screw can include any pitch known and used in the art, and may be chosen to maximize efficiency of the actuator. In some embodiments, one or more of roller screw threads and ball screw threads may be incorporated into the design to improve lead screw 312 efficiency. Additionally, the instant embodiment includes a threaded insert 311 made out of a softer material than the lead screw 312, which also improves overall efficiency of the electric motor 331.

Figure 5D:
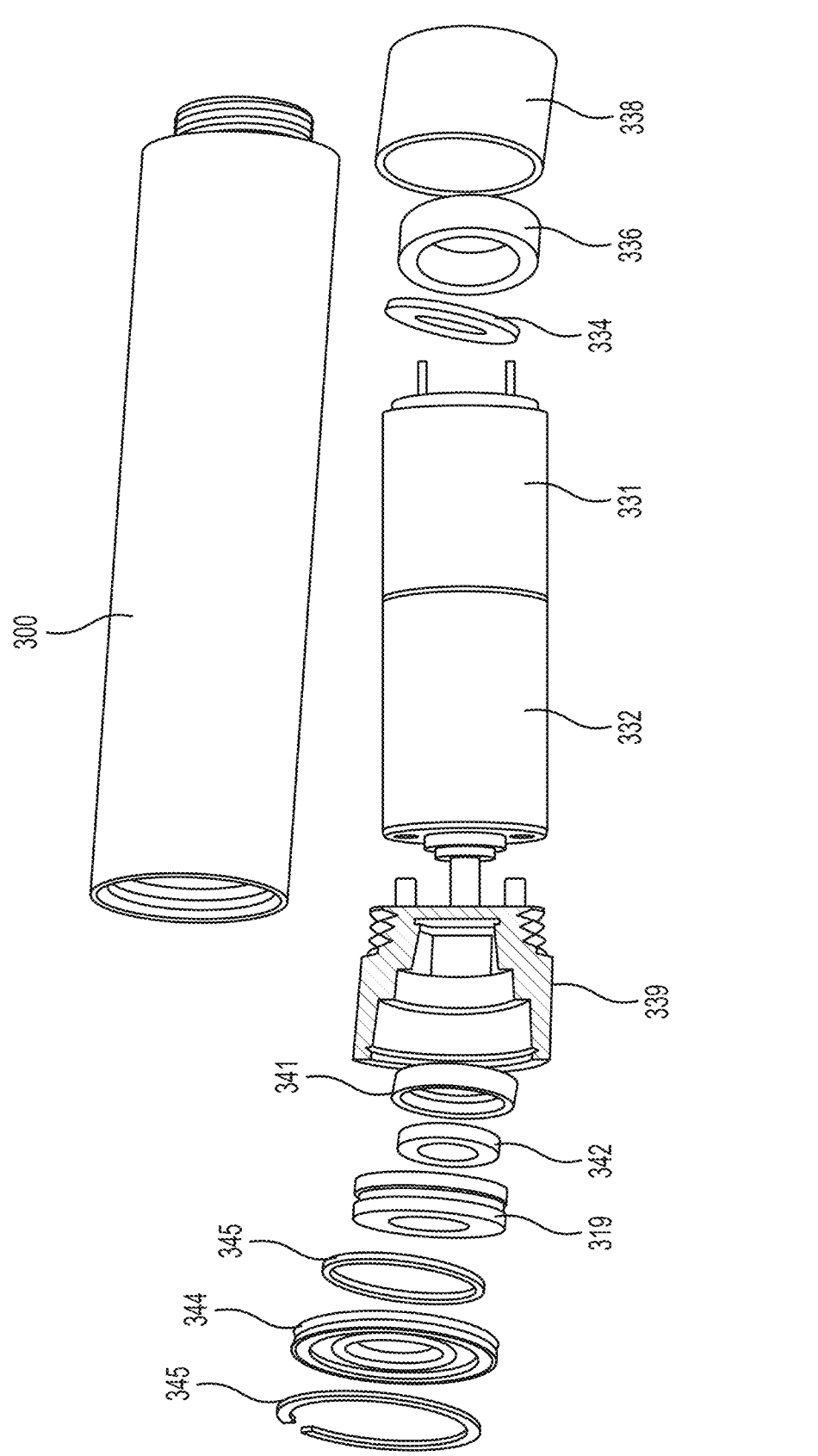

FIG. 5D shows an exploded view of some of the interior components of the implant 300. The container 330 shown including a cap 339 configured to secure the electric motor 331, the gear housing 332, the controller 334, the ultrasonic transducer 336, and the power storage device 338. The container 330 may additionally house a chassis 335 to vertically arrange the circuitry operably connecting the components. The retainer capture sleeve 341, the two-piece primary tension retainer 342, the thrust bearing 319, and the low friction bi-directional seal assembly 344 including the two snap rings 345 are shown.

The retainer capture sleeve 341 is sometimes called an anti-jam plate and is secured with respect to the shaft by the retainer 342. The retainer capture sleeve 341 communicates some of the distraction forces from the lead screw 312 to the first thrust bearing 319, which may communicate some of the distraction forces onto the cap 339. This results in less axial distraction forces being placed on the electric motor 331.

FIGS. 6A-6G illustrate an adjustable implant 400 in accordance with a fourth embodiment. Like the above mentioned embodiments, the adjustable implant 400 is configured for bi-directional ultrasonic communication. The adjustable implant 400 includes an actuator operatively coupled to an ultrasonic transducer configured for transcutaneous bidirectional ultrasonic data communication. The adjustable implant 300 is configured to be controlled by an external transceiver 900 and configured to send and receive ultrasound signals, including, for example, modulated ultrasound waves.

As one with skill in the art may appreciate, many of the components previously introduced can be used with the instant embodiment. In some cases, the components may be identical between this embodiment and the previous embodiments and are illustrated with similar reference numbers numbering in the 400s. The various parts, features, and components disclosed herein are interchangeable and the various features of each embodiment may be communicated to the other embodiments enumerated herein, with the full breadth of this disclosure limited by the claims.

Figures 6A, 6B:
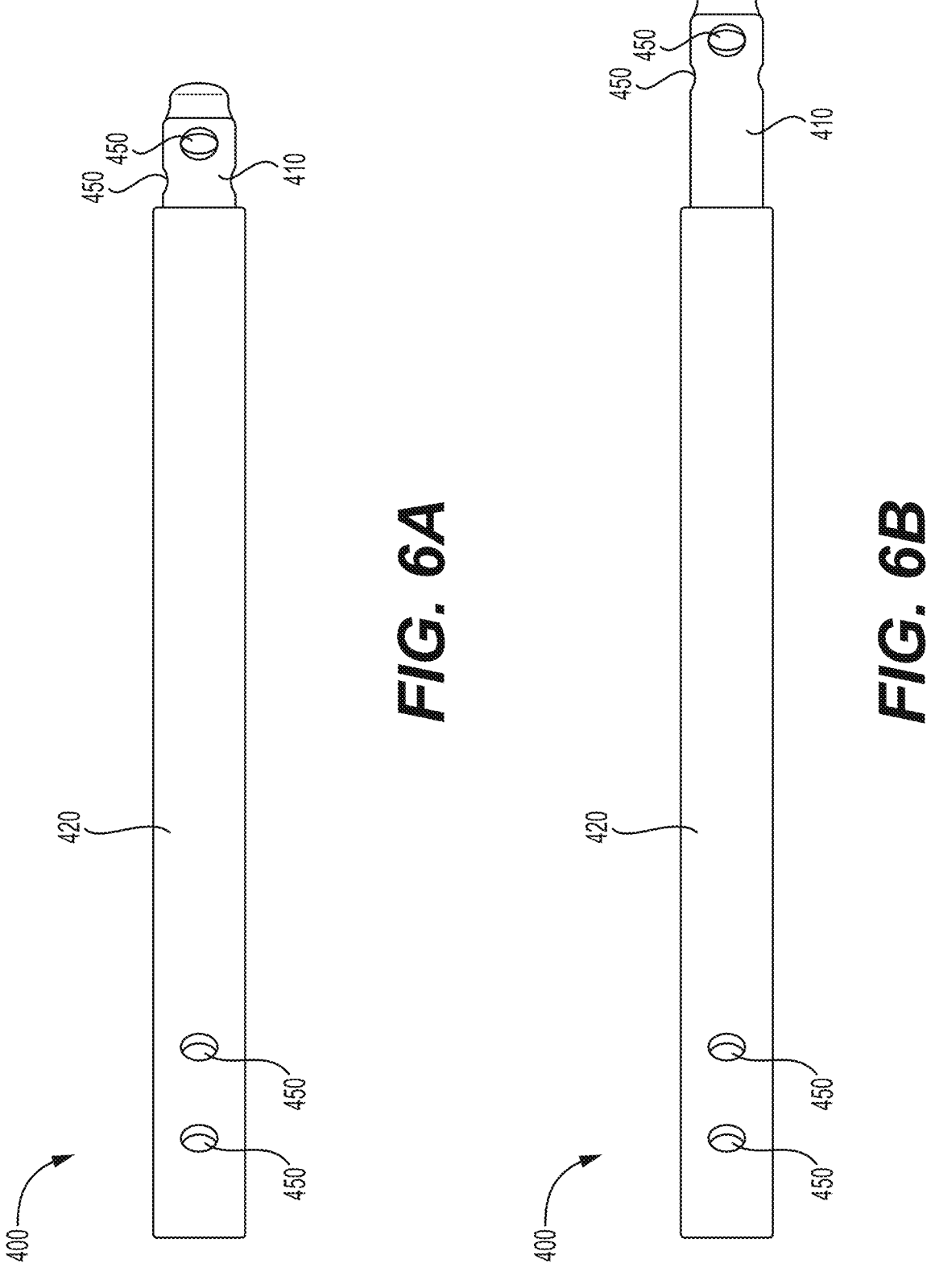
FIG. 6A shows a side view of an adjustable implant in accordance with a fourth embodiment, the adjustable implant shown in a first retracted configuration.
FIG. 6B shows a side view of the adjustable implant in accordance with the fourth embodiment, the adjustable implant shown in a second expanded configuration.

FIG. 6A shows a side view of the adjustable implant 400 in a first retracted configuration with at least a portion of a rod 410 telescopically received within an outer housing 420. In this embodiment, the adjustable implant 400 is an intramedullary rod configured to treat a bone of a patient. The rod 410 is configured to be telescopically received in and displaced from the outer housing 420 by the actuator. In some embodiments, this adjustable implant 400 may be configured to treat another skeletal deformity, for example, a distraction rod configured to be mounted to a plurality of vertebrae and configured to treat scoliosis.

In this embodiment, the outer housing 420 and the rod 410 include apertures 450 dimensioned to receive bone fixation devices there through, with the bone fixation devices configured to secure the adjustable implant 400 with respect to a skeletal system of a patient. The bone fixation devices may include bone screws, hooks, pins, rods, and any device known and used to secure an implant with respect to a patient's skeletal structure.

FIG. 6B shows a side view of the adjustable implant 400 in a second distracted configuration with the rod 410 shown telescopically displaced from the outer housing 420.

Figure 6C:
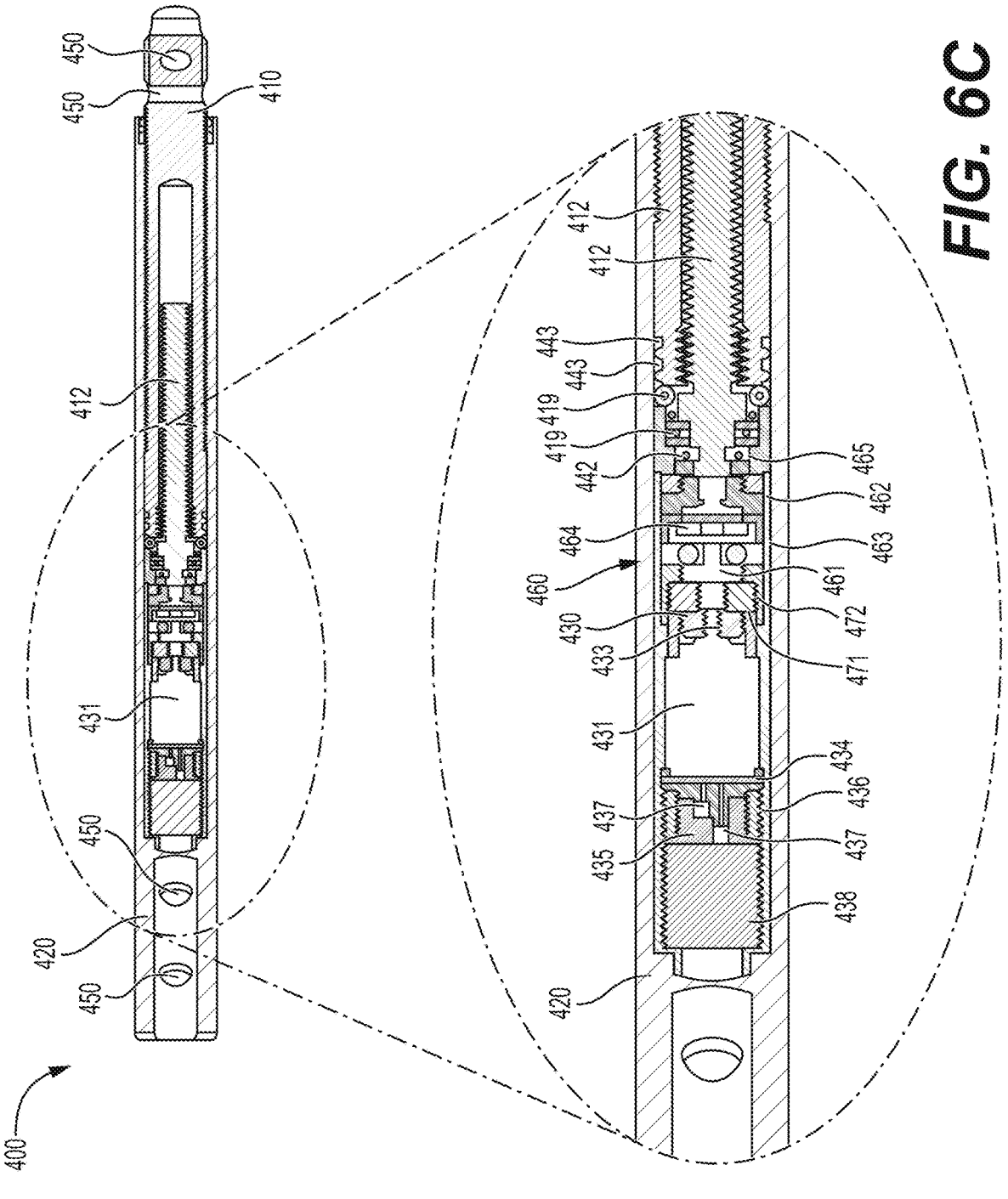
FIG. 6C shows a cross-sectional side view of the adjustable implant in accordance with the fourth embodiment, with an enhanced portion of the adjustable implant provided for convenience.

FIG. 6C shows a cross-sectional side view of the adjustable implant 400 along with an enhanced view of some of the interior components of the adjustable implant 400. In this embodiment, the rod 410 includes a cavity having an at least partially threaded interior surface configured to communicate with a lead screw 412. The at least partially threaded interior surface may include a thread disposed directly on an interior surface of the rod 410. In this embodiment, a threaded insert 411 is secured to the interior of the rod 410 by, for example, an epoxy. The threaded insert 411 may include a material different than the rod 410. In some embodiments, the threaded insert 411 may be made of a biocompatible thermoplastic, e.g. polyether ether ketone (PEEK), polyether ketone (PEK), and/or a biocompatible metal, e.g., titanium. Using a material for the threaded insert 411 that is softer than the lead screw 412 helps prevent binding and improves efficiency of the actuator.

In this embodiment, the threaded insert 411 is made of a thermoplastic material, e.g., polyether ether ketone (PEEK), and the lead screw 412 is made of a biocompatible metal, e.g., stainless steel. As discussed above, using a softer material for the threaded insert can reduce binding and improve efficiency of the electric motor 431.

The lead screw 412 is configured to rotate and displace the rod 410 relative to outer housing 420 upon a rotation of the lead screw 412 by an actuator. Rotation of the lead screw 412 causes a communication between a threaded surface of the lead screw with a threaded surface of the rod 410. As one with skill in the art may appreciate, depending upon the direction of rotation of the lead screw 412, the lead screw 412 may move the rod 410 into or out of the outer housing 420.

The adjustable implant 400 includes an actuator. In this embodiment, the actuator is an electric motor 431. The electric motor 431 is operably connected to a gear housing 432 which may include one or more planetary gear sets configured to transfer rotational motion from the output of the electric motor 431 to the lead screw 412.

The electric motor 431 is operably coupled to a controller 434. The controller 434 is also operably coupled to an ultrasonic transducer 436 and a power storage device 438. The ultrasonic transducer 436 in this embodiment includes a hollow cylindrical ultrasonic transducer 436 configured to contact a periphery of the adjustable implant 400. The controller 434 may include a printed circuit board and may be configured for integration in a stacked configuration relative to the ultrasonic transducer 436 and the power storage device 438, with the electrical connections being established through a chassis 435 via interconnects 437.

In this embodiment, a hermetic seal contains the power storage device 438 and the electric motor 431 within the adjustable implant 400, specifically hermetically sealing them within a container 430. The hermetic seal includes a container and a through-wall coupling which, in this embodiment, includes a magnetic coupling configured to transfer rotational motion from the electric motor 431 contained within the container 430, to the lead screw 412 located outside of the container 430. The magnetic coupling includes a first magnet 471 operably coupled to an output of the electric motor 431, with the electric motor 431 configured to rotate the first magnet 471. The magnetic coupling allows the electric motor 431 and the power storage device 438 to stay hermetically sealed within the container 430.

In this embodiment, the magnetic coupling is achieved with the second magnet 472 annularly disposed around at least a portion of the first magnet 471. In this embodiment, the second magnet 472 has a ring shape (see FIG. 6F). In some embodiments, one or more magnets may be placed adjacent to the first magnet 471 and may rotate with the first magnet 471, for example, one or more coaxially with and circumferentially around the first magnet 471. In some embodiments, the first magnet 471 may be placed adjacent to the second magnet 472 along the axis of the adjustable implant, and the first magnet 471 may rotate simultaneously with the second magnet 472.

This embodiment includes a gear housing 432. The gear housing 432 may include one or more planetary gear sets. For example, in some embodiments, the gear housing may include: one, two, three and more planetary gear sets. The gear housing 432 is configured to reduce the rotary speed from the actuator and increase an amount of torque delivered at the lead screw 412.

In this embodiment, the second magnet 472 is coupled to the sun gear of a first planetary gear set 461. Upon actuation of the electric motor 431, the electric motor 431 will rotate the first magnet 471. The first magnet 471 is magnetically coupled to the second magnet 472, thereby transferring torque to the second magnet 472 from inside the hermetically sealed container 430 and thereby rotating the second magnet 472. Rotation of the second magnet 472 engages the first planetary gear set 461 which engages at least one ring gear 463. The at least one ring gear 463 engages a second planetary gear set 462, with the second planetary gear set 462 configured to rotate a drive stage 465. A first end of the drive stage 465 is configured to communicate with the sun gear of the second planetary gear set 462, with the second end of the drive stage 465 keyed and configured to couple with the lead screw 412. In this embodiment, the keyed end of the drive stage 465 includes a hexagonal profile configured to communicate with a hexagonal profile of the lead screw 412. As one with skill in the art may appreciate, in some embodiments, the drive stage 465 and the lead screw 412 may include any geometrical profile as long as the drive stage can translate rotational motion to the lead screw 412. For example, the drive stage may include one or more of a triangular, a rectangular, a star, and any other known profile configured to mate with a corresponding profile of a lead screw. The magnetic coupling enables torque to transfer through the wall of the container 430 from the inside of the container 430 to the outside of the container 430, keeping the container 430 hermetically sealed, and allowing, for example, some non-bio-compatible materials to be stored inside the container in some embodiments.

In some embodiments, each ring gear 463 is configured to maintain the output of gear housing 432 and reduce an overall axial length of the gear housing 432. This may help provide a shorter total length of the adjustable implant, which is extremely useful in, for example, pediatrics. In some embodiments, the ring gear 463 may include a floating ring gear 464. The floating ring gear 464 may be designed with more teeth than the fixed ring gear, thereby compounding the gear ratio to eliminate at least one sun gear of one gear housing. This again reduces a total axial length of the adjustable implant 400 and thereby helping enable, for example, the adjustable implant 400 to be used in smaller patients, such as pediatrics.

In some embodiments, the gear housing 432 includes three planetary gear sets. The three planetary gear sets include three sun gears. As one with skill in the art may appreciate, a gear set with three sun gears has a relatively long length. A ring gear 464, specifically a floating ring gear 464 in place of one sun gear reduces the overall length of the gear housing 432, thereby reducing a total axial length of the adjustable implant 400 and thereby helping enable, for example, the adjustable implant 400 to be used in smaller patients, such as pediatrics.

The adjustable implant 400 may include one or more of: at least one thrust bearing 419 and a retainer capture sleeve 441, each configured to reduce an amount of axial load on the electronic motor 431 and the gear housing 432. These features divert axial load placed on the lead screw 412 from the actuator to one or more of the container 430 and housing 420.

In this embodiment, the encapsulated components of the container 430 assembly are disposed within a hollow interior cavity of the outer housing 420. As discussed above, the interior components of the container 430 are hermetically sealed therein. In this embodiment, additional layers of encapsulation are provided by, for example, at least one O-ring 443 disposed between the outer housing 420 and the rod 410

As one with skill in the art may appreciate, in some embodiments, the adjustable implant 400 may include any and all of the various ultrasonic communication features and capabilities as further described throughout this disclosure. For example, one or more of the electric motor 431 and the controller 434 may be configured to send and receive data via ultrasonic communication using the ultrasonic transducer 436. In some embodiments, the data may include adjustment instructions for the actuator. In some embodiments, the adjustment instructions include active control of the actuator. Additionally, in some embodiments, the data transmitted across the ultrasonic communication link may be related to the patient including, for example, data corresponding to a biological condition.

Using an electronic motor 431 to drive the adjustable implant 400 includes being able to monitor current draw of the electric motor 431 to determine an amount of force applied by the adjustable implant 400. In this embodiment, the controller 434 may monitor the current draw of the electric motor 431 and determine an amount of force applied to the bone of the patient. Similar to FIG. 2, the controller 434 may communicate the amount of force to an external transceiver 900 using the ultrasonic transducer 436. And the external transceiver 900 and/or a tertiary device 910 may use this information to calculate new distraction instructions for the adjustable implant 400 and communicate the new distraction instructions to the adjustable implant 400 using an ultrasonic signal.

In some embodiments, the lead screw 412 may include a thread pitch chosen and configured to minimize an amount of energy consumed by the electric motor 431 to move the rod 310 relative to the outer housing 420. In some embodiments, the pitch of the lead screw 412 may be chosen to optimize efficiency of the electric motor 431. The lead screw 412 efficiency determines an amount of power consumption and indirectly defines a size of the power storage device 438. Maximizing lead screw 412 efficiency minimizes power consumption and allows for use of a smaller power storage device 438, thereby, minimizing a size of the adjustable implant 400. In this embodiment, a lead screw pitch of 20 threads per inch (tpi) is chosen for the small diameter lead screw 412. A lead screw pitch of 20 tpi is four times more efficient than, for example, a lead screw pitch of 80 tpi. In some embodiments, one or more of roller screw threads and ball screw threads may be incorporated into the design to improve lead screw 412 efficiency. Additionally, the instant embodiment includes a threaded insert 411 made out of a softer material than the lead screw 412, which also improves overall efficiency of the electric motor 431.

Figure 6D:
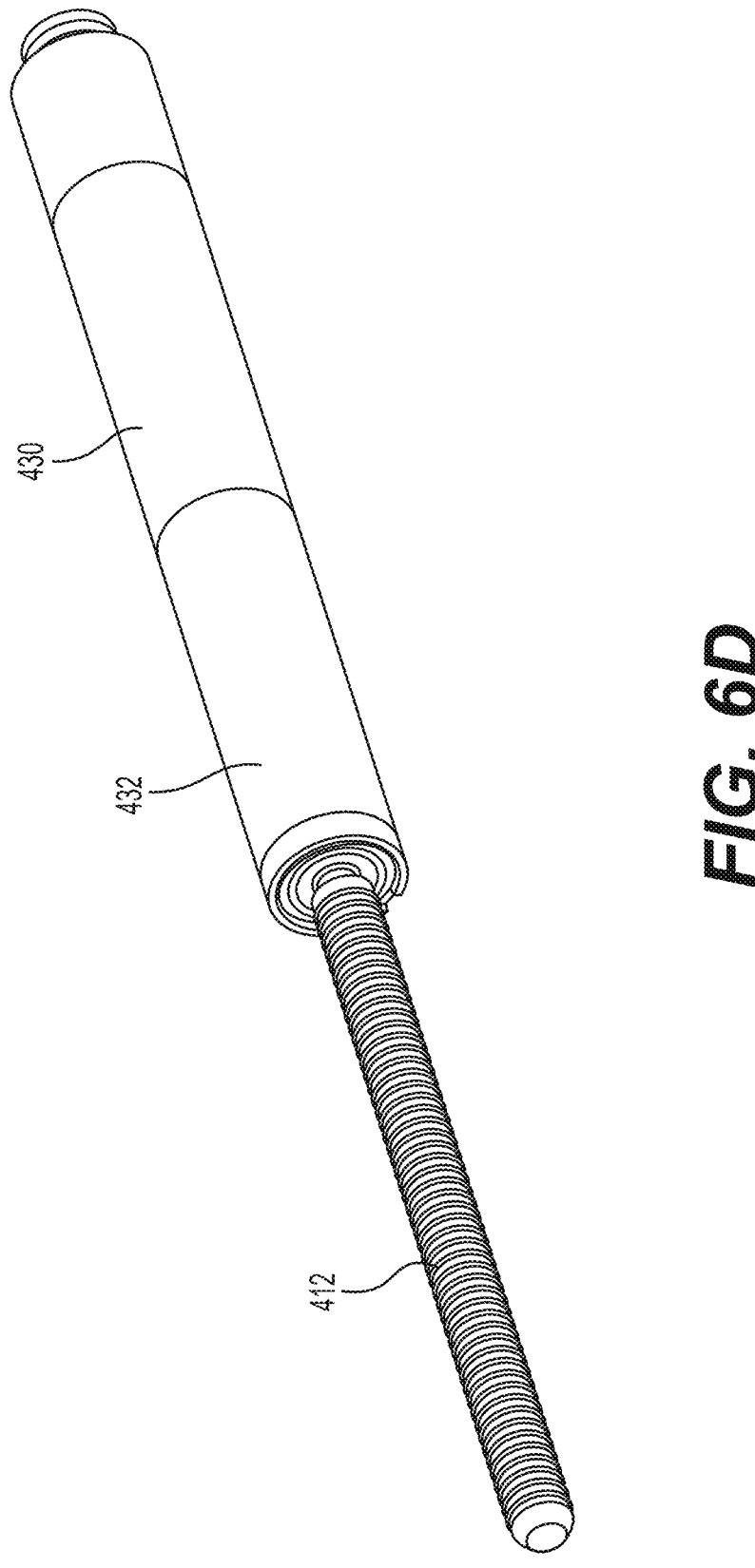
FIG. 6D shows a perspective view of the actuator and the gear stage coupled to the lead screw.
Figures 6E, 6F:
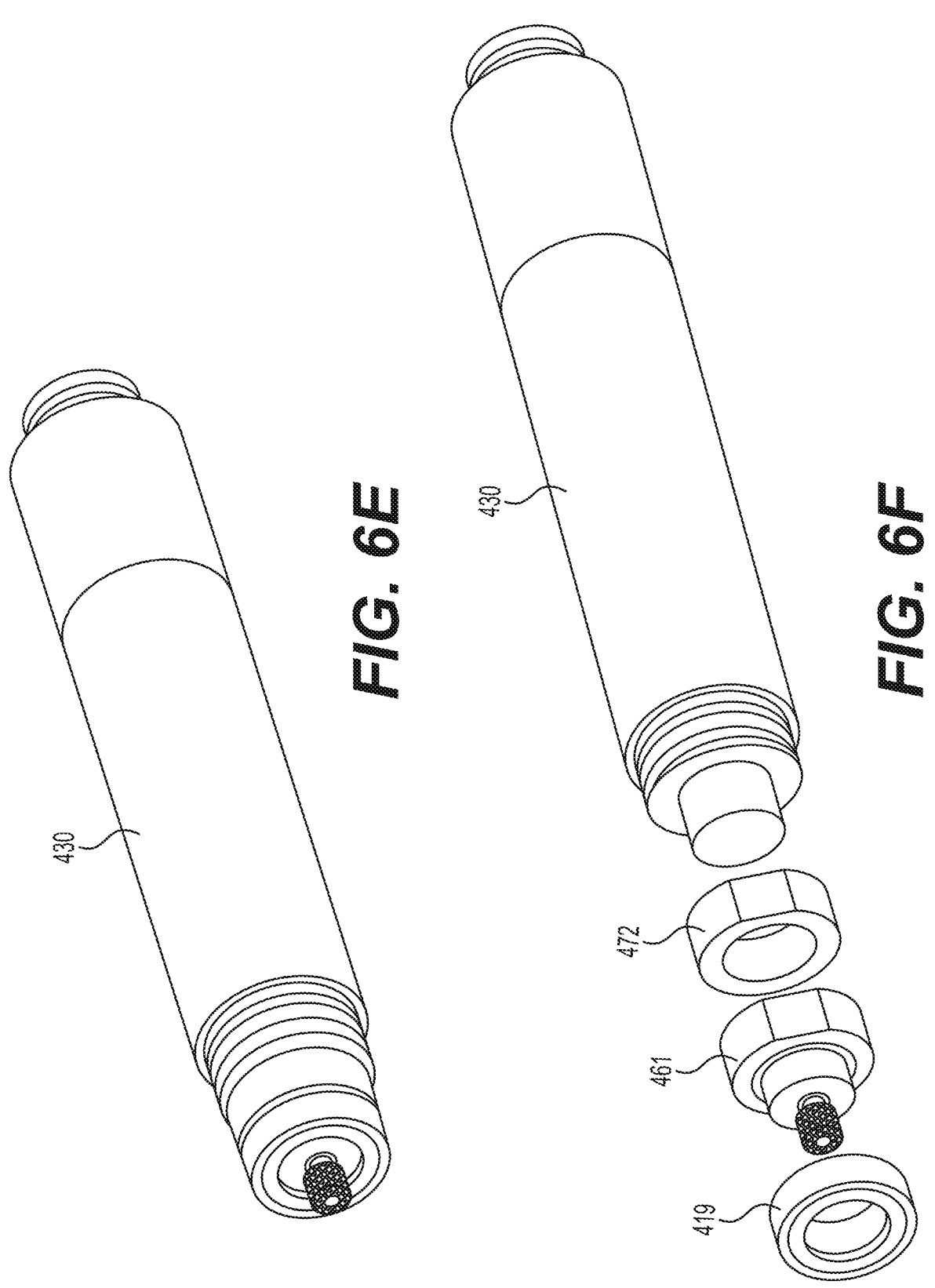
FIG. 6E shows a perspective view of the container and the magnetic coupling.
FIG. 6F shows an exploded view of the container and the magnetic coupling.

FIG. 6D shows a perspective view of the lead screw 412 coupled to the actuator. In this embodiment, the actuator includes an electric motor 431 hermetically contained within a container 430, and a housing stage 432. FIG. 6E shows the container 430 of the electric motor 431 coupled to a sun gear of a first planetary gear set 461 by a magnetic coupling. FIG. 6F is an exploded view of the magnetic coupling, with the second magnet 472 shown displaced from the container 430.

As discussed above, the magnetic coupling includes a first magnet 471 located within the container 430 magnetically coupled to a second magnet 472 located outside of the container 430. The magnetic coupling is configured to transfer torque from the electric motor 431 hermetically contained within the container 430, to the gear housing 432 located outside of the container 430. In some embodiments, the gear housing 432 may also be hermetically contained within the container 430, with the magnetic coupling configured to transfer torque from the gear housing 432 to, for example, the lead screw 412. As one with skill in the art may appreciate, the magnetic coupling can be moved up and down the chain of torque from the electric motor to the rod, this disclosure is intended to pertain to all possible embodiments.

Figure 6G:
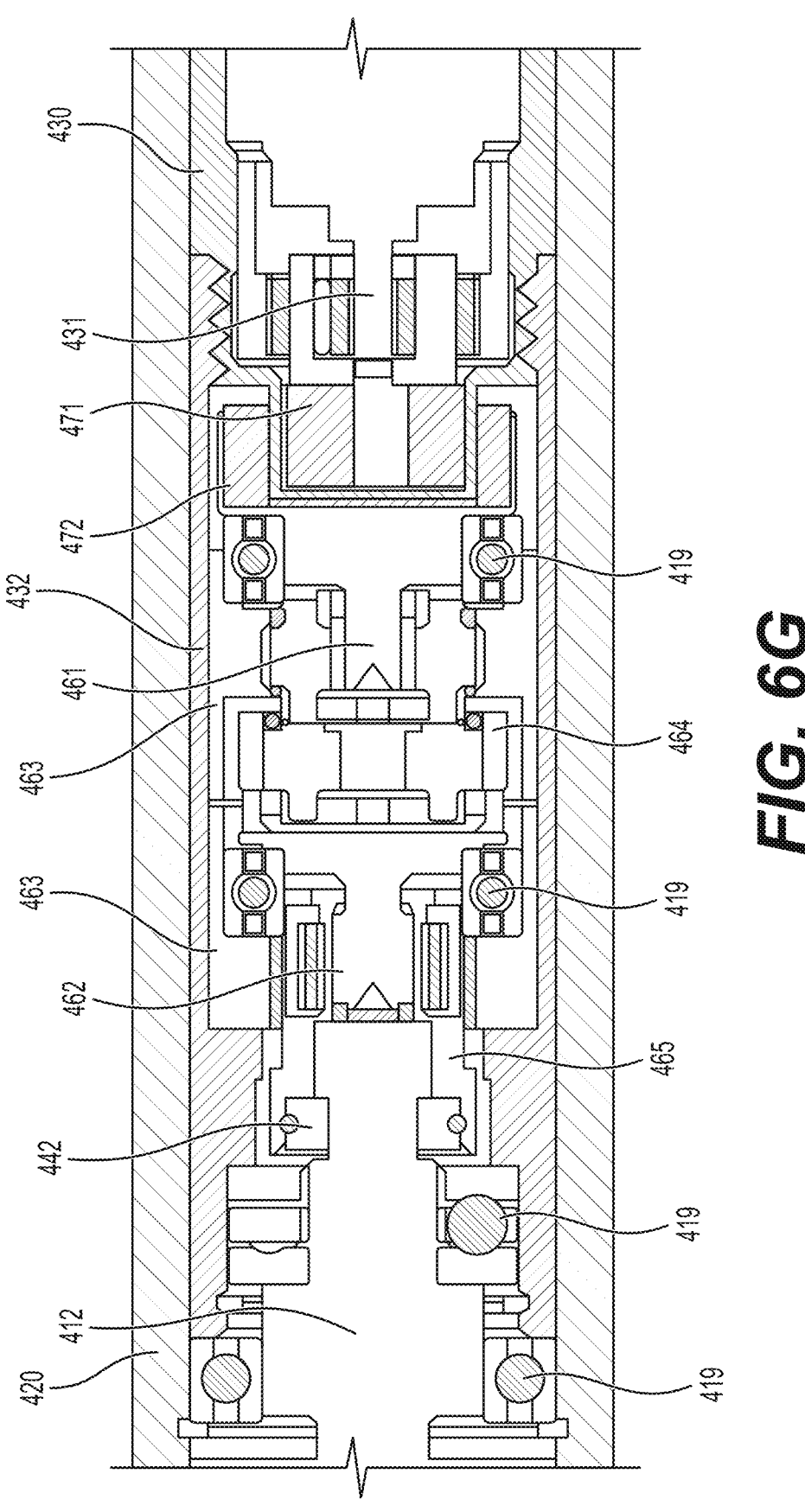
FIG. 6G shows a cross sectional side view of the adjustable implant showing the electric motor coupled to the lead screw.
Figure 6H:
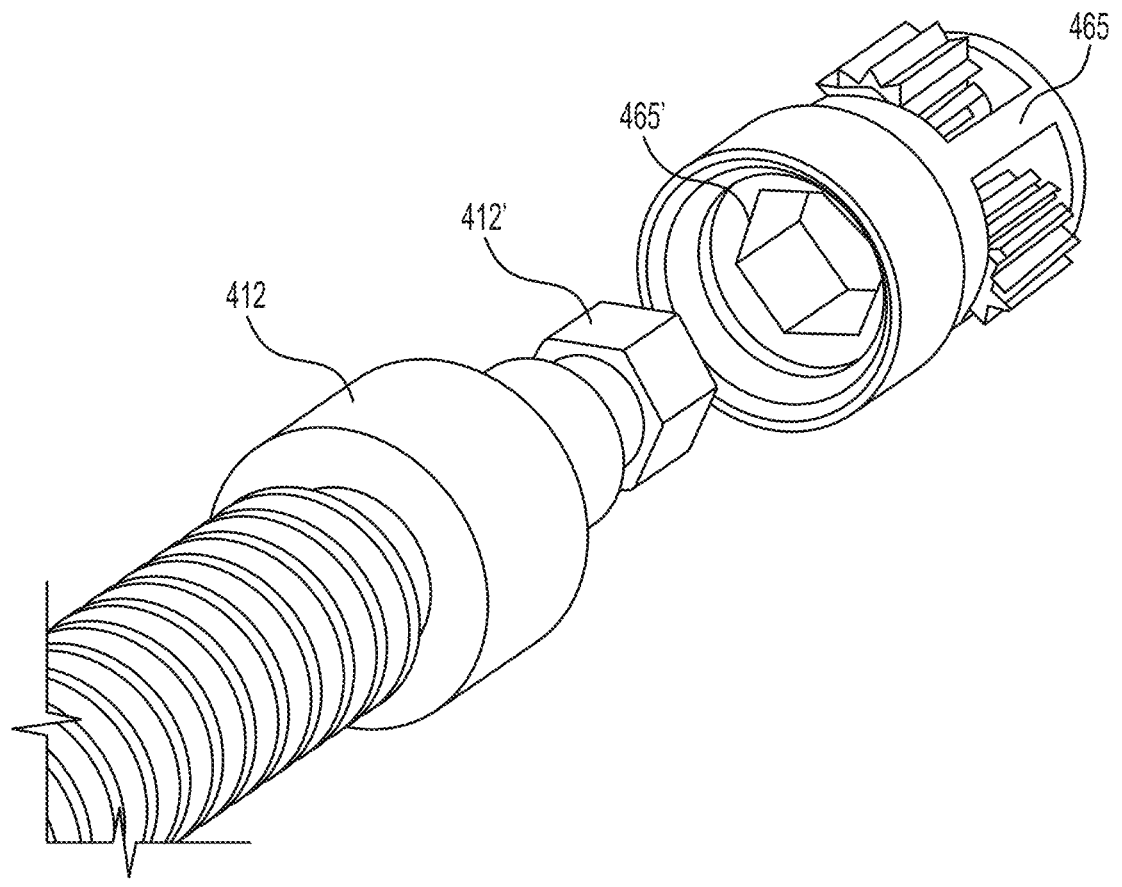
FIG. 6H shows a coupling of the drive stage to the lead screw.

FIG. 6G shows an enhanced cross-sectional view of the gear housing 432 coupling the lead screw 412 to the electric motor 431. In this embodiment, the second magnet 472 is coupled to the sun gear of a first planetary gear set 461. The electric motor 431 may be controlled locally by the controller 434, or may be controlled remotely from one or more of an external transceiver 900 and a tertiary device 910 using, for example, one or more of the ultrasound communication techniques enumerated above. Upon actuation of the electric motor 431, the electric motor 431 will rotate the first magnet 471. The first magnet 471 is disposed within the container 430 and magnetically coupled to the second magnet 472 located outside of the container 430, thereby transferring torque to the second magnet 472 from inside the hermetically sealed container 430 and thereby rotating the second magnet 472. Rotation of the second magnet 472 engages the first planetary gear set 461 which engages at least one ring gear 463. The at least one ring gear 463 engages a second planetary gear set 462, with the second planetary gear set 462 configured to rotate a drive stage 465. In this embodiment, the drive stage 465 includes a hex drive stage 465. The hex drive stage 465 includes a hexagonal profile 465' configured to communicate with a lead screw having a hexagonal profile 412'. As one with skill in the art may appreciate, other geometries for both may be chosen, including friction fit circular, star-shaped, keyed, triangular, rectangular, hexagonal, and the like, such that rotation of the drive stage 465 rotates the lead screw. A first end of the hex drive stage 465 is configured to communicate with the sun gear of the second planetary gear set 462, with the second end of the hex drive stage 465 configured to couple with the lead screw 412.

The adjustable implant 400 may include one or more of: at least one thrust bearing 419 and a retainer capture sleeve

441 each configured to reduce an amount of axial load on the electronic motor 431 and the gear housing 432. These features divert axial load placed on the lead screw 412 from the actuator to one or more of the container 430 and housing 420. The container 430 may sit within the outer housing 420, and may include one or more abutments upon which one or more of the thrust bearings 419 may be disposed. Additionally, the outer housing 420 may include one or more abutments configured to hold one of the thrust bearings 419.

The container 430 is shown including the electric motor 431, the controller 434, the ultrasonic transducer 436, and the power storage device 438. The container 430 may additionally house a chassis 435 configured to vertically arrange the components and circuitry operably connecting the components via interconnects 437. The retainer capture sleeve 441, the two-piece primary tension retainer 442, the thrust bearing 419, and the low friction bi-directional seal assembly 444 including the two snap rings 445 are shown. Snap rings 445 and any known retaining components or fixtures may be included.

In some embodiments, a safety feature includes preprogramming one or more of the controller 434 and the external transceiver 900 with instructions configured to prevent actuation of the electric motor 431 in a state where an ultrasonic data communication link is broken. For example, in a first state with the external controller not in communication with the controller 434, the controller prevents the electric motor 431 from being actuated. In a second state, with the external controller in communication with the controller 434, the controller allows the electric motor 431 from being actuated. This type of control hand-shake protocol prevents the electric motor 431 from adjusting the adjustable implant, when not under direct control from the external transceiver.

In some embodiments, a continuous drive shaft may be used to transfer torque through the adjustable implant from the actuator to the lead screw. In some embodiments, a plurality of gear sets may be added. In some embodiments, planetary gear sets may be used. In some embodiments, strain wave gear systems and harmonic drives may be used. In some embodiments, an impact driver may be used to transfer torque through the adjustable implant.

Figure 7:
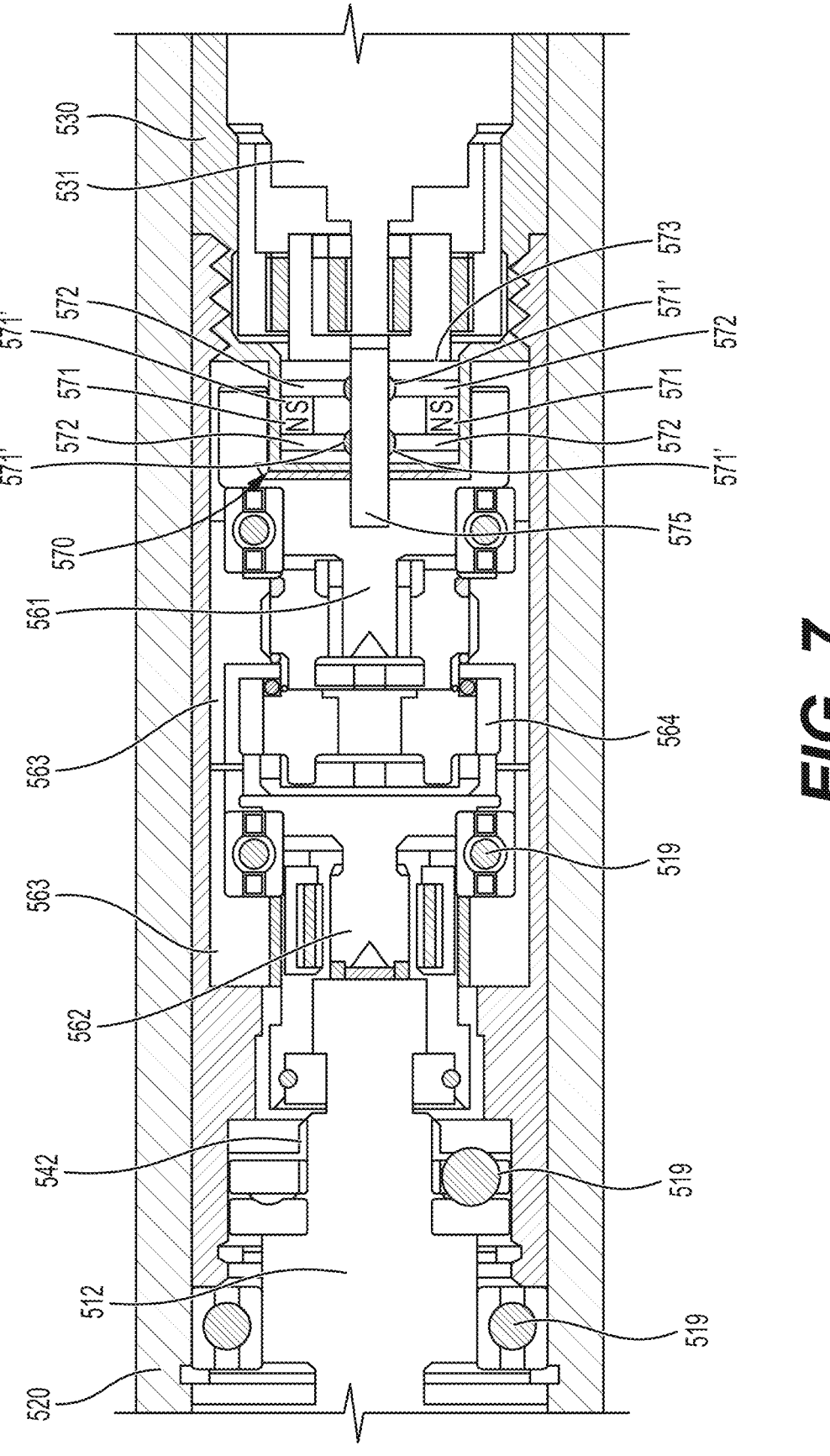
FIG. 7 shows a cross sectional side view of an adjustable implant in accordance with a fifth embodiment, the adjustable implant including a magnetic fluid seal.

FIG. 7 shows a cross-sectional view of an adjustable implant 500 in accordance with a fifth embodiment. The adjustable implant includes a gear housing 532 coupling the lead screw 512 to the electric motor 531. In this embodiment, the first sun gear 561 of the gear housing 532 is coupled to the electric motor 431 by a fluid seal 570. The fluid seal is a magnetic fluid seal 570. The magnetic fluid seal includes a casing 573, a plurality of pole shoes 572 made out of ferromagnetic material, a permanent magnet 571, a magnetic fluid 571', and a shaft 575 made of a ferromagnetic material. The shaft 575 is coupled to the electric motor 531 and the first sun gear 561 of the gear housing 532. The casing 573 and the pole shoes 572 are coupled to the container 530, with a space separating the shaft from the pole shoes 572. The magnetic fluid 571' is disposed on or around the shaft 575 filling the space between the shaft 575 and the pole shoes 572. As the shaft 575 rotates, the magnetic fluid 571' will continue to fill the space between the pole shoes 572. This hermetically seals the interior components of the container 530 therein, while allowing torque to be transferred out of the container 430 by the shaft 575.

Note, that some embodiments may include some of the same features as other embodiments. Accordingly, similar components share similar reference numbers with the hundreds digit changed to correspond to a specific illustrated embodiment. As one with skill in the art may appreciate, and unless noted otherwise, shared components may not be introduced in every embodiment but are identifiable by their reference numbers in similar embodiments.

Various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present processes, machines, manufacture, composition of matter, means, methods, or steps, presently existing or later to be developed that perform the function or achieve the result as the corresponding embodiments described herein may be utilized according to the present disclosure.

What is claimed is:

1. An adjustable implant comprising:
a first portion configured to be secured to a bone at a first location;
a second portion configured to telescopically receive the first portion and configured to be secured to a bone at a second location;
an actuator configured to move the first portion relative to the second portion;
an ultrasonic transducer operably coupled to the actuator and configured to communicate with an external transceiver using ultrasound signals;
a container having a hermetic seal containing the actuator therein; and
wherein the container further comprises a magnetic coupling having a first magnet rotatably coupled to the actuator and disposed within the container, and a second magnet disposed outside the container configured to magnetically couple to and rotate with the first magnet wherein a rotation of the first magnet rotates the second magnet.

2. The adjustable implant of claim 1, wherein a rotation of the second magnet is configured to move the first portion relative to the second portion.

3. The adjustable implant of claim 1, the ultrasonic transducer comprising a hollow piezoelectric transducer.

4. The adjustable implant of claim 1, the actuator comprising an electric motor.

5. The adjustable implant of claim 1, further comprising a power storage device.

6. The adjustable implant of claim 5, wherein the power storage device is charged using electrical energy harvested from an ultrasonic signal.

7. The adjustable implant of claim 1, comprising a controller operably connected to one or more of the ultrasonic transducer and the actuator.

8. The adjustable implant of claim 7, wherein the controller is configured to receive adjustment instructions via the ultrasonic transducer and actuate the actuator according to the adjustment instructions.

9. The adjustable implant of claim 8, wherein the controller is configured to communicate data to the external transceiver using ultrasound signals.

10. An adjustable implant comprising:
a rod configured to be secured to a bone at a first location;
a housing configured to telescopically receive the rod and configured to be secured to a bone at a second location;
an actuator disposed in the housing configured to move the rod relative to the housing;
an ultrasonic transducer operably coupled to th;e actuator and configured to communicate with an external transceiver using ultrasound waves
a power storage device and a container configured to seal one or more of the actuator and the power storage device therein; and
wherein the container comprises a magnetic coupling configured to transfer torque out of the container.

11. The adjustable implant of claim 10, the actuator comprising an electric motor.

12. The adjustable implant of claim 10, wherein the power storage device is configured to be charged using electrical energy from an ultrasound signal.

13. The adjustable implant of claim 10, comprising a controller operably connected to at least one of the ultrasonic transducer and the actuator.

14. The adjustable implant of claim 13, wherein the controller is configured to receive adjustment instructions via the ultrasonic transducer and actuate the actuator according to the adjustment instructions.

15. The adjustable implant of claim 13, wherein the controller is configured to communicate data associated with the actuator to the external transceiver using ultrasound waves.

16. The adjustable implant of claim 10, comprising a gear housing having at least one planetary gearset.

17. The adjustable implant of claim 16, comprising a floating ring gear.

*     *     *     *     *